(12) United States Patent
Nakajima et al.

(10) Patent No.: US 9,766,241 B2
(45) Date of Patent: Sep. 19, 2017

(54) PGC-1BETA-PROTEIN-FUNCTION REGULATOR, MITOCHONDRIA-FUNCTION REGULATOR, ANTI-OBESITY AGENT, AND SCREENING METHOD THEREFOR

(71) Applicant: Toshihiro Nakajima, Yokohama-shi, Kanagawa (JP)

(72) Inventors: Toshihiro Nakajima, Yokohama (JP); Hidetoshi Fujita, Chofu (JP); Satoko Aratani, Tokyo (JP); Naoko Yagishita, Yokohama (JP)

(73) Assignee: Toshihiro Nakajima, Yokohama-shi, Kanagawa (JP)

( * ) Notice: Subject to any disclaimer, the term of this patent is extended or adjusted under 35 U.S.C. 154(b) by 1 day.

(21) Appl. No.: 14/655,744

(22) PCT Filed: Dec. 26, 2013

(86) PCT No.: PCT/JP2013/084960
§ 371 (c)(1),
(2) Date: Aug. 3, 2015

(87) PCT Pub. No.: WO2014/104224
PCT Pub. Date: Jul. 3, 2014

(65) Prior Publication Data
US 2015/0330981 A1    Nov. 19, 2015

(30) Foreign Application Priority Data

Dec. 26, 2012  (JP) ................. 2012-283766
Jul. 22, 2013  (JP) ................. 2013-152094

(51) Int. Cl.
| | | |
|---|---|---|
| G01N 33/53 | (2006.01) | |
| G01N 33/573 | (2006.01) | |
| G01N 33/68 | (2006.01) | |
| G01N 33/50 | (2006.01) | |
| C12Q 1/68 | (2006.01) | |

(52) U.S. Cl.
CPC ......... *G01N 33/573* (2013.01); *C12Q 1/6883* (2013.01); *G01N 33/5044* (2013.01); *G01N 33/6875* (2013.01); *C12Q 2600/136* (2013.01); *C12Q 2600/158* (2013.01); *G01N 2333/70567* (2013.01); *G01N 2333/9015* (2013.01); *G01N 2440/36* (2013.01); *G01N 2500/04* (2013.01); *G01N 2500/10* (2013.01)

(58) Field of Classification Search
None
See application file for complete search history.

(56) References Cited

FOREIGN PATENT DOCUMENTS

| | | |
|---|---|---|
| JP | 2002-080362 A | 3/2002 |
| JP | 2005-514921 A | 5/2005 |
| JP | 2008-074753 A | 4/2008 |
| JP | 2008-517931 A | 5/2008 |
| JP | 2011-001311 A | 1/2011 |
| JP | 2012-524033 A | 10/2012 |
| JP | WO2012176860 A1 | 12/2012 |
| KR | WO2009031842 A1 | 3/2009 |

OTHER PUBLICATIONS

International Search Report of international patent application No. PCT/JP2013/084960 completed on Feb. 6, 2014 and mailed Feb. 18, 2014 ( 2 pages ).
Nieman D C et al., "Quercetin's Influence on Exercise Performance and Muscle Mitochondrial Biogenesis", Med Sci Sports Exerc, vol. 42, No. 2, p. 338-345, 2010.
Ahn J et al., "The anti-obesity effect of quercetin is mediated by the AMPK and MAPK signaling pathways" Biochem Biophys Res Commun, vol. 373, No. 4, p. 545-549, 2008.
St-Pierre J et al., "Bioenergetic analysis of peroxisome proliferator-activated receptor gamma coactivators 1alpha and 1beta (PGC-1alpha and PGC-1beta) in muscle cells", J Biol Chem, vol. 278, No. 29, p. 26597-26603, 2003.
Kamei Y et al., "PPARgamma coactivator 1 beta/ERR ligand 1 is an ERR protein ligand, whose expression induces a high-energy expenditure and antagonizes obesity", Proc Natl Acad Sci USA, vol. 100, No. 21, p. 12378-12383, 2003.
Viana Abranches et al., "Peroxisome proliferator-activated receptor: effects on nutritional homeostasis, obesity and diabetes mellitus", 2011.
Ulf Andersson et al., "PGC-1-Related Coactivator, a Novel, Serum-Inducible Coactivator of Nuclear Respiratory Factor 1-Dependent Transcription in Mammalian Cells", 2001.
Dieter Kressler et al., "The PGC-1-related Protein PERC Is a Selective Coactivator of Estrogen Receptor α*",2002.
Jiandie Lin et al., "Peroxisome Proliferator-activated Receptor Y Coactivator 1β (PGC-1β), A Novel PGC-1-related Transcription Coactivator Associated with Host Cell Factor*", 2001.

*Primary Examiner* — Celine Qian
(74) *Attorney, Agent, or Firm* — Pyprus Pte Ltd

(57) ABSTRACT

[Problem]
To provide a mitochondria-function regulator effective for treatment or prevention of obesity, and a screening method therefore.
[Solution]
The mitochondria-function regulator of the present invention contains, as an active ingredient, a PGC-1β-protein function regulator synoviolin. The screening method of the present invention includes a step for causing a test substance to act on an adipose tissue cell or an individual animal, and measuring or detecting one or more of the following in the adipose tissue cell: (1) expression level of synoviolin; (2) a bond between synoviolin and PGC-1β protein; and (3) the ubiquitination of the PGC-1β protein by synoviolin.

2 Claims, 19 Drawing Sheets

Fig. 20

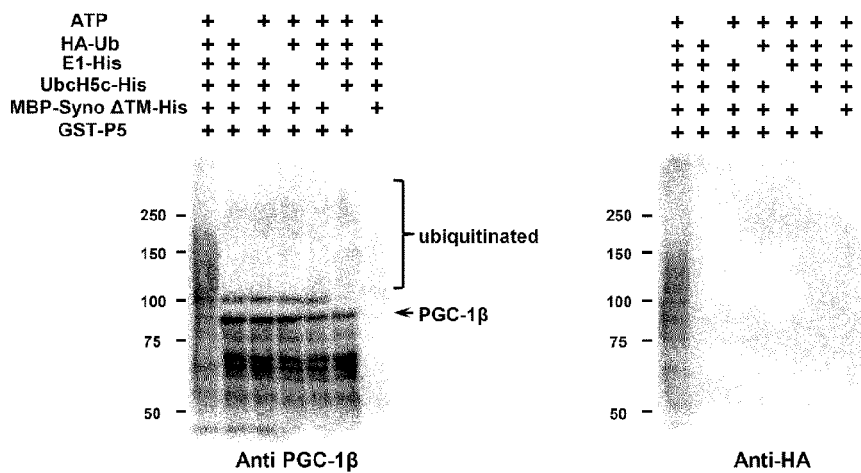

Fig. 21

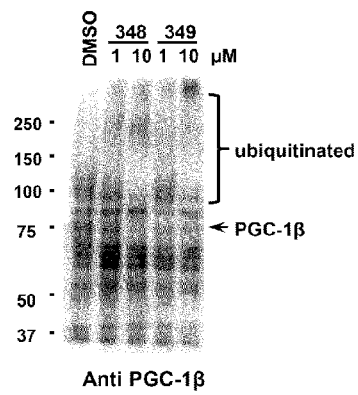

Fig. 22

|  | Seq. |  | 236 | 241 | 246 | 251 | 256 | 261 | 266 | 270 | Identity |
|---|---|---|---|---|---|---|---|---|---|---|---|
| 47 | H. sapiens | | K V H T F | P L F A I | R P M Y L | A M R Q - F | K K A - - - V T | D A I M S | R - - R A I R | | 100 % |
| 48 | M. musculus | | K V H T F | P L F A I | R P M Y L | A M R Q - F | K K A - - - V T | D A I M S | R - - R A I R | | 100 % |
| 49 | X. laevis | | K V H T F | P L F A I | R P M Y L | A M R Q - F | K K A - - - V T | D A I M S | R - - R A I R | | 100 % |
| 50 | D. rerio | | K V H T F | P L F A I | R P M Y L | A M R Q - F | K K A - - - V T | D A I M S | R - - R A I R | | 100 % |
| 51 | D. melanogaster | | K I Y A L | P M F V F | R P M F F | T I R N - F | K A - - - L N | D V I M S | R - - R A I R | | 54.2 % |
| 52 | C. elegans | | K V H T F | P L F S V | R P F Y Q | S V R A - L | H K A - - - F L | D V I L S | R - - R A I N | | 57.14 % |
| 53 | S. cerevisiae | | A I D V F | P R F L R | T A L H L | S M L I P F | R M P M M - L L | K D V V W | D - - - - I L | | 16.7 % |

```
                        SEQUENCE LISTING

<160> NUMBER OF SEQ ID NOS: 53

<210> SEQ ID NO 1
<211> LENGTH: 3374
<212> TYPE: DNA
<213> ORGANISM: Homo sapiens

<400> SEQUENCE: 1
gccctttctt atgagcatgc ctgtgttggg ttgacagtga gggtaataat gacttgttgg      60
ttgattgtag atatagggct ctcccttgca aggtaattag gctccttaaa ttacctgtaa     120
gattttcttg ccacagcatc cattctggtt aggctggtga tcttctgagt agtgatagat     180
tggttggtgg tgaggtttac aggtgttccc ttctcttact cctggtgttg gctacaatca     240
ggtggcgtct agagcagcat gggacaggtg ggtaagggga gtcttctcat tatgcagaag     300
tgatcaactt aaatctctgt cagatctacc tttatgtagc ccggcagtcg cgcggattga     360
```

```
gcgggctcgc ggcgctgggt tcctggtctc cgggccaggg caatgttccg cacggcagtg      420
atgatggcgg ccagcctggc gctgaccggg gctgtggtgg ctcacgccta ctacctcaaa      480
caccagttct accccactgt ggtgtacctg accaagtcca gccccagcat ggcagtcctg      540
tacatccagg cctttgtcct tgtcttcctt ctgggcaagg tgatgggcaa ggtgttcttt      600
gggcaactga gggcagcaga gatggagcac cttctggaac gttcctggta cgccgtcaca      660
gagacttgtc tggccttcac cgttttcgg gatgacttca gccccgctt tgttgcactc       720 ttcactcttc ttctcttcct caaatgtttc cactggctgg ctgaggaccg tgtggacttt      780
atggaacgca gccccaacat ctcctggctc tttcactgcc gcattgtctc tcttatgttc      840
ctcctgggca tcctggactt cctcttcgtc agccacgcct atcacagcat cctgacccgt      900
ggggcctctg tgcagctggt gtttggcttt gagtatgcca tcctgatgac gatggtgctc      960
accatcttca tcaagtatgt gctgcactcc gtggacctcc agagtgagaa ccccctgggac    1020 aacaaggctg tgtacatgct ctacacagag ctgtttacag gcttcatcaa ggttctgctg     1080
tacatggcct tcatgaccat catgatcaag gtgcacacct tcccactctt tgccatccgg     1140
cccatgtacc tggccatgag acagttcaag aaagctgtga cagatgccat catgtctcgc     1200
cgagccatcc gcaacatgaa caccctgtat ccagatgcca cccagagga gctccaggca     1260 atggacaatg tctgcatcat ctgccgagaa gagatggtga ctggtgccaa gagactgccc     1320
tgcaaccaca ttttccatac cagctgcctg cgctcctggt tccagcggca gcagacctgc     1380
cccacctgcc gtatggatgt ccttcgtgca tcgctgccag cgcagtcacc accaccccg      1440 gagcctgcgg atcagggccc accccctgcc ccccacccc caccactctt gcctcagccc     1500
cccaacttcc cccagggcct cctgcctcct tttcctccag gcatgttccc actgtggccc    1560
cccatgggcc ccttttccacc tgtcccgcct cccccagct caggagaggc tgtggctcct    1620
ccatccacca gtgcagcagc ccttcctcgg cccagtggag cagctacaac acagctgct    1680 ggcaccagtg ctactgctgc ttctgccaca gcatctggcc caggctctgg ctctgcccca    1740
gaggctggcc ctgcccctgg tttcccttc cctcctccct ggatgggtat gcccctgcct    1800
ccaccctttg ccttccccc aatgcctgtg ccccctgcgg gctttgctgg gctgacccca    1860
gaggagctac gagctctgga gggccatgag cggcagcacc tggaggcccg gctgcagagc    1920
ctgcgtaaca tccacacact gctggacgcc gccatgctgc agatcaacca gtacctcacc    1980
gtgctggcct ccttggggcc ccccggcct gccacttcag tcaactccac tgagggact     2040 gccactacag ttgttgctgc tgcctcctcc accagcatcc ctagctcaga ggccacgacc    2100
ccaaccccag gagcctcccc accagcccct gaaatggaaa ggcctccagc tcctgagtca    2160
gtgggcacag aggagatgcc tgaggatgga gagcccgatg cagcagagct ccgcggcgc    2220 cgcctgcaga agctggagtc tcctgttgcc cactgacact gccccagccc agccccagcc    2280
tctgctcttt tgagcagccc tcgctggaac atgtcctgcc accaagtgcc agctccctct    2340
ctgtctgcac cagggagtag taccccccagc tctgagaaag aggcggcatc ccctaggcca    2400
agtggaaaga ggctggggtt cccatttgac tccagtccca ggcagccatg gggatctcgg    2460
gtcagttcca gccttcctct ccaactcttc agccctgtgt tctgctgggg ccatgaaggc    2520
agaaggttta gcctctgaga agccctcttc ttcccccacc cctttccagg agaaggggct    2580 gccccctccaa gccctacttg tatgtgcgga gtcacactgc agtgccgaac agtattagct    2640
cccgttccca agtgtggact ccagaggggc tggaggcaag ctatgaactt gctcgctggc    2700
```

```
ccaccccctaa gactggtacc catttccttt tcttaccctg atctccccag aagcctcttg    2760
tggtggtggc tgtgcccct atgcctgtg gcatttctgc gtcttactgg caaccacaca      2820
actcagggaa aggaatgcct gggagtgggg gtgcaggcgg gcagcactga gggaccctgc    2880
cccgcccctc cccccaggcc cctttcccct gcagcttctc aagtgagact gacctgtctc    2940
acccagcagc cactgcccag ccgcactcca ggcaagggcc agtgcgcctg ctcctgacca    3000
ctgcaatccc agcgcccaag gaaggccact tctcaactgg cagaacttct gaagtttaga    3060
attggaatta cttccttact agtgtctttt ggcttaaatt ttgtcttttg aagttgaatg    3120
cttaatcccg ggaaagagga acaggagtgc cagactcctg gtctttccag tttagaaaag    3180
gctctgtgcc aaggagggac cacaggagct gggacctgcc tgcccctgtc ctttcccctt    3240
ggttttgtgt tacaagagtt gttggagaca gtttcagatg attatttaat ttgtaaatat    3300
tgtacaaatt ttaatagctt aaattgtata tacagccaaa taaaaacttg cattaacaaa    3360
aaaaaaaaaa aaaa                                                      3374
```

<210> SEQ ID NO 2
<211> LENGTH: 19
<212> TYPE: RNA
<213> ORGANISM: Artificial Sequence
<220> FEATURE:
<223> OTHER INFORMATION: Synthetic RNA

<400> SEQUENCE: 2
gcugugacag augccauca                                                 19

<210> SEQ ID NO 3
<211> LENGTH: 19
<212> TYPE: RNA
<213> ORGANISM: Artificial Sequence
<220> FEATURE:
<223> OTHER INFORMATION: Synthetic RNA

<400> SEQUENCE: 3
gguguucuuu gggcaacug                                                 19

<210> SEQ ID NO 4
<211> LENGTH: 19
<212> TYPE: RNA
<213> ORGANISM: Artificial Sequence
<220> FEATURE:
<223> OTHER INFORMATION: Synthetic RNA

<400> SEQUENCE: 4
gguucugcug uacauggcc                                                 19

<210> SEQ ID NO 5
<211> LENGTH: 19
<212> TYPE: RNA
<213> ORGANISM: Artificial Sequence
<220> FEATURE:
<223> OTHER INFORMATION: Synthetic RNA

<400> SEQUENCE: 5
cguuccuggu acgccguca                                                 19

<210> SEQ ID NO 6
<211> LENGTH: 18
<212> TYPE: RNA
<213> ORGANISM: Artificial Sequence
<220> FEATURE:
<223> OTHER INFORMATION: Synthetic RNA

<400> SEQUENCE: 6
guuuggugac uggugcua                                                       18

<210> SEQ ID NO 7
<211> LENGTH: 19
<212> TYPE: RNA
<213> ORGANISM: Artificial Sequence
<220> FEATURE:
<223> OTHER INFORMATION: Synthetic RNA

<400> SEQUENCE: 7
auggugacug gugcuaaga                                                      19

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ccggtcaatg ccatcagt                                                       18

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ctaaccgtat ggtccaaact agc                                                 23

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
ctacggacag accgagtgc                                                      19

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tttacataat tgcaaggcat gg                                                  22

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
actgtcaccc cagcgaac                                                       18

<210> SEQ ID NO 13

```
<211> LENGTH: 24
<212> TYPE: DNA
<213> ORGANISM: Artificial Sequence
<220> FEATURE:
<223> OTHER INFORMATION: Primer

<400> SEQUENCE: 13
ccaggagact attcttgcta aagg                                            24

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
agattgggcc tatagggaag a                                               21

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
caccgggagg taccaagaa                                                  19

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
cccaaaacag tatcccaatc at                                              22

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
taagagaccc cgtagccatc                                                 20

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
ccaaagaagc agcgatgg                                                   18

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
```
tagagctcag gcagggtga                                                    19

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gacaagctgg atcaggcaag                                                   20

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
gaggccacag aggctgttc                                                    19

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
tccaggcgaa cgtgactt                                                     18

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
cagaggtttc tgccatgcta                                                   20

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
accttcccgc tggacact                                                     18

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ggcaatcctt ctgttttgc                                                    20

<210> SEQ ID NO 26
<211> LENGTH: 20
<212> TYPE: DNA

<213> ORGANISM: Artificial Sequence
<220> FEATURE:
<223> OTHER INFORMATION: Primer

<400> SEQUENCE: 26
agcctgagac ctcaaagcag                                              20

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
ccttcaatcg gcaagacg                                                18

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tacccaacct tggctagacg                                              20

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
gtccgaggag agagcttgc                                               19

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
ccgagggctc tgtcatca                                                18

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
gggcagctga ctgaggaa                                                18

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
ggaaagacaa cggacaaatc a                                            21

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
attcggatgg ccacctct                                                     18

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
tgtggaactc tctggaactg c                                                 21

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
agggttatct tggttggctt ta                                                22

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
ctccagttcc ggctcctc                                                     18

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
ccctctgctc tcacgtctg                                                    19

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
aaaccatgac cgaagtagcc                                                   20

<210> SEQ ID NO 39
<211> LENGTH: 23
<212> TYPE: DNA
<213> ORGANISM: Artificial Sequence
<220> FEATURE:

<223> OTHER INFORMATION: Primer

<400> SEQUENCE: 39
aggccagttg tgatgactaa gac                                    23

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
ccagccaaaa ctcccactt                                         19

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
gaaccatgaa gccaacgac                                         19

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
ggacgtgctg tacaatgagg                                        20

<210> SEQ ID NO 43
<211> LENGTH: 18
<212> TYPE: DNA
<213> ORGANISM: Artificial Sequence
<220> FEATURE:
<223> OTHER INFORMATION: Primer

<400> SEQUENCE: 43
gcatgccaca tacgcagt                                          18

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
tggagtccaa gatgctaatg g                                      21

<210> SEQ ID NO 45
<211> LENGTH: 18
<212> TYPE: DNA
<213> ORGANISM: Artificial Sequence
<220> FEATURE:
<223> OTHER INFORMATION: Primer

<400> SEQUENCE: 45
gcgaggctgg ttaccaca                                          18

-continued

```
<210> SEQ ID NO 46
<211> LENGTH: 601
<212> TYPE: PRT
<213> ORGANISM: Homo sapiens

<400> SEQUENCE: 46
```

| Met | Phe | Arg | Thr | Ala | Val | Met | Met | Ala | Ala | Ser | Leu | Ala | Leu | Thr | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Val | Val | Ala | His | Ala | Tyr | Tyr | Leu | Lys | His | Gln | Phe | Tyr | Pro | Thr |
|-----|-----|-----|-----|-----|-----|-----|-----|-----|-----|-----|-----|-----|-----|-----|-----|
|     |     |     | 20  |     |     |     | 25  |     |     |     |     | 30  |     |     |     |

| Val | Val | Tyr | Leu | Thr | Lys | Ser | Ser | Pro | Ser | Met | Ala | Val | Leu | Tyr | Ile |
|     |     |     | 35  |     |     |     |     | 40  |     |     |     | 45  |     |     |     |

| Gln | Ala | Phe | Val | Leu | Val | Phe | Leu | Leu | Gly | Lys | Val | Met | Gly | Lys | Val |
|     | 50  |     |     |     |     |     | 55  |     |     |     |     | 60  |     |     |     |

| Phe | Phe | Gly | Gln | Leu | Arg | Ala | Ala | Glu | Met | Glu | His | Leu | Leu | Glu | Arg |
| 65  |     |     |     |     | 70  |     |     |     |     | 75  |     |     |     |     | 80  |

| Ser | Trp | Tyr | Ala | Val | Thr | Glu | Thr | Cys | Leu | Ala | Phe | Thr | Val | Phe | Arg |
|     |     |     |     | 85  |     |     |     |     | 90  |     |     |     |     | 95  |     |

| Asp | Asp | Phe | Ser | Pro | Arg | Phe | Val | Ala | Leu | Phe | Thr | Leu | Leu | Leu | Phe |
|     |     |     |     | 100 |     |     |     |     | 105 |     |     |     |     | 110 |     |

| Leu | Lys | Cys | Phe | His | Trp | Leu | Ala | Glu | Asp | Arg | Val | Asp | Phe | Met | Glu |
|     |     |     |     | 115 |     |     |     |     | 120 |     |     |     |     | 125 |     |

| Arg | Ser | Pro | Asn | Ile | Ser | Trp | Leu | Phe | His | Cys | Arg | Ile | Val | Ser | Leu |
|     | 130 |     |     |     |     | 135 |     |     |     |     | 140 |     |     |     |     |

| Met | Phe | Leu | Leu | Gly | Ile | Leu | Asp | Phe | Leu | Phe | Val | Ser | His | Ala | Tyr |
| 145 |     |     |     |     | 150 |     |     |     |     | 155 |     |     |     |     | 160 |

| His | Ser | Ile | Leu | Thr | Arg | Gly | Ala | Ser | Val | Gln | Leu | Val | Phe | Gly | Phe |
|     |     |     |     |     | 165 |     |     |     |     | 170 |     |     |     |     | 175 |

| Glu | Tyr | Ala | Ile | Leu | Met | Thr | Met | Val | Leu | Thr | Ile | Phe | Ile | Lys | Tyr |
|     |     |     | 180 |     |     |     |     | 185 |     |     |     |     | 190 |     |     |

| Val | Leu | His | Ser | Val | Asp | Leu | Gln | Ser | Glu | Asn | Pro | Trp | Asp | Asn | Lys |
|     |     |     | 195 |     |     |     |     | 200 |     |     |     |     | 205 |     |     |

| Ala | Val | Tyr | Met | Leu | Tyr | Thr | Glu | Leu | Phe | Thr | Gly | Phe | Ile | Lys | Val |
|     | 210 |     |     |     |     | 215 |     |     |     |     | 220 |     |     |     |     |

| Leu | Leu | Tyr | Met | Ala | Phe | Met | Thr | Ile | Met | Ile | Lys | Val | His | Thr | Phe |
| 225 |     |     |     |     | 230 |     |     |     |     | 235 |     |     |     |     | 240 |

| Pro | Leu | Phe | Ala | Ile | Arg | Pro | Met | Tyr | Leu | Ala | Met | Arg | Gln | Phe | Lys |
|     |     |     |     | 245 |     |     |     |     | 250 |     |     |     |     | 255 |     |

| Lys | Ala | Val | Thr | Asp | Ala | Ile | Met | Ser | Arg | Arg | Ala | Ile | Arg | Asn | Met |
|     |     |     | 260 |     |     |     |     | 265 |     |     |     |     | 270 |     |     |

| Asn | Thr | Leu | Tyr | Pro | Asp | Ala | Thr | Pro | Glu | Glu | Leu | Gln | Ala | Met | Asp |
|     |     |     | 275 |     |     |     |     | 280 |     |     |     |     | 285 |     |     |

| Asn | Val | Cys | Ile | Ile | Cys | Arg | Glu | Glu | Met | Val | Thr | Gly | Ala | Lys | Arg |
|     | 290 |     |     |     |     | 295 |     |     |     |     | 300 |     |     |     |     |

| Leu | Pro | Cys | Asn | His | Ile | Phe | His | Thr | Ser | Cys | Leu | Arg | Ser | Trp | Phe |
| 305 |     |     |     |     | 310 |     |     |     |     | 315 |     |     |     |     | 320 |

| Gln | Arg | Gln | Gln | Thr | Cys | Pro | Thr | Cys | Arg | Met | Asp | Val | Leu | Arg | Ala |
|     |     |     |     | 325 |     |     |     |     | 330 |     |     |     |     | 335 |     |

| Ser | Leu | Pro | Ala | Gln | Ser | Pro | Pro | Pro | Glu | Pro | Ala | Asp | Gln | Gly |     |
|     |     |     | 340 |     |     |     |     | 345 |     |     |     |     | 350 |     |     |

| Pro | Pro | Pro | Ala | Pro | His | Pro | Pro | Leu | Leu | Pro | Gln | Pro | Pro | Asn |     |
|     |     |     |     | 355 |     |     |     |     | 360 |     |     |     |     | 365 |     |

| Phe | Pro | Gln | Gly | Leu | Leu | Pro | Phe | Pro | Pro | Gly | Met | Phe | Pro | Leu |     |
|     | 370 |     |     |     |     | 375 |     |     |     |     | 380 |     |     |     |     |

```
Trp Pro Pro Met Gly Pro Phe Pro Val Pro Pro Ser Ser
385                 390                 395                 400

Gly Glu Ala Val Ala Pro Pro Ser Thr Ser Ala Ala Leu Ser Arg
                405                 410                 415

Pro Ser Gly Ala Ala Thr Thr Thr Ala Ala Gly Thr Ser Ala Thr Ala
                420                 425                 430

Ala Ser Ala Thr Ala Ser Gly Pro Gly Ser Gly Ser Ala Pro Glu Ala
                435                 440                 445

Gly Pro Ala Pro Gly Phe Pro Phe Pro Pro Pro Trp Met Gly Met Pro
            450                 455                 460

Leu Pro Pro Pro Phe Ala Phe Pro Pro Met Pro Val Pro Pro Ala Gly
465                 470                 475                 480

Phe Ala Gly Leu Thr Pro Glu Glu Leu Arg Ala Leu Glu Gly His Glu
                485                 490                 495

Arg Gln His Leu Glu Ala Arg Leu Gln Ser Leu Arg Asn Ile His Thr
            500                 505                 510

Leu Leu Asp Ala Ala Met Leu Gln Ile Asn Gln Tyr Leu Thr Val Leu
            515                 520                 525

Ala Ser Leu Gly Thr Val Val Ala Ala Ser Ser Thr Ser Ile Pro
            530                 535                 540

Ser Ser Glu Ala Thr Thr Pro Thr Pro Gly Ala Ser Pro Ala Pro
545                 550                 555                 560

Glu Met Glu Arg Pro Pro Ala Pro Glu Ser Val Gly Thr Glu Met
                565                 570                 575

Pro Glu Asp Gly Glu Pro Asp Ala Ala Glu Leu Arg Arg Arg Leu
            580                 585                 590

Gln Lys Leu Glu Ser Pro Val Ala His
            595                 600

<210> SEQ ID NO 47
<211> LENGTH: 35
<212> TYPE: PRT
<213> ORGANISM: Homo sapiens

<400> SEQUENCE: 47

Lys Val His Thr Phe Pro Leu Phe Ala Ile Arg Pro Met Tyr Leu Ala
1               5                   10                  15

Met Arg Gln Phe Lys Lys Ala Val Thr Asp Ala Ile Met Ser Arg Arg
            20                  25                  30

Ala Ile Arg
        35

<210> SEQ ID NO 48
<211> LENGTH: 35
<212> TYPE: PRT
<213> ORGANISM: Mus musculus

<400> SEQUENCE: 48

Lys Val His Thr Phe Pro Leu Phe Ala Ile Arg Pro Met Tyr Leu Ala
1               5                   10                  15

Met Arg Gln Phe Lys Lys Ala Val Thr Asp Ala Ile Met Ser Arg Arg
            20                  25                  30

Ala Ile Arg
        35

<210> SEQ ID NO 49
<211> LENGTH: 35
```

```
<212> TYPE: PRT
<213> ORGANISM: Xenopus laevis

<400> SEQUENCE: 49

Lys Val His Thr Phe Pro Leu Phe Ala Ile Arg Pro Met Tyr Leu Ala
1               5                   10                  15

Met Arg Gln Phe Lys Lys Ala Val Thr Asp Ala Ile Met Ser Arg Arg
            20                  25                  30

Ala Ile Arg
        35

<210> SEQ ID NO 50
<211> LENGTH: 35
<212> TYPE: PRT
<213> ORGANISM: Danio rerio

<400> SEQUENCE: 50

Lys Val His Thr Phe Pro Leu Phe Ala Ile Arg Pro Met Tyr Leu Ala
1               5                   10                  15

Met Arg Gln Phe Lys Lys Ala Val Thr Asp Ala Ile Met Ser Arg Arg
            20                  25                  30

Ala Ile Arg
        35

<210> SEQ ID NO 51
<211> LENGTH: 35
<212> TYPE: PRT
<213> ORGANISM: Drosophila melanogaster

<400> SEQUENCE: 51

Lys Ile Tyr Ala Leu Pro Met Phe Val Phe Arg Pro Met Phe Phe Thr
1               5                   10                  15

Ile Arg Asn Phe Arg Lys Ala Leu Asn Asp Val Ile Met Ser Arg Arg
            20                  25                  30

Ala Ile Arg
        35

<210> SEQ ID NO 52
<211> LENGTH: 35
<212> TYPE: PRT
<213> ORGANISM: Caenorhabditis elegans

<400> SEQUENCE: 52

Arg Val His Thr Phe Pro Leu Phe Ser Val Arg Pro Phe Tyr Gln Ser
1               5                   10                  15

Val Arg Ala Leu His Lys Ala Phe Leu Asp Val Ile Leu Ser Arg Arg
            20                  25                  30

Ala Ile Asn
        35

<210> SEQ ID NO 53
<211> LENGTH: 36
<212> TYPE: PRT
<213> ORGANISM: Saccharomyces cerevisiae

<400> SEQUENCE: 53

Ala Ile Asp Val Phe Thr Arg Phe Leu Lys Thr Ala Leu His Leu Ser
1               5                   10                  15

Met Leu Ile Pro Phe Arg Met Pro Met Met Leu Leu Lys Asp Val Val
            20                  25                  30
```

Trp Asp Ile Leu
      35

PGC-1BETA-PROTEIN-FUNCTION REGULATOR, MITOCHONDRIA-FUNCTION REGULATOR, ANTI-OBESITY AGENT, AND SCREENING METHOD THEREFOR

TECHNICAL FIELD

The present invention relates to a PGC-1β-protein-function regulator, a mitochondria-function regulator, an anti-obesity agent, and a screening method therefor.

BACKGROUND ART

Nuclear receptors and their coactivators are thought to play central roles in mitochondria biogenesis and in energy metabolism including cellular respiration and β-oxidation of fatty acids. Peroxisome proliferator-activated receptors (PPARs) compose the nuclear receptor superfamily having three isoforms of PPARα, PPARβ/δ, and PPARγ (see Non-Patent Literature 1). PGC-1α, PGC-1β, and PGC-1-related coactivator (PRC) are known as three coactivators for PPAR (see Non-Patent Literatures 2 to 4).

PGC-1β overexpression results in an increased mitochondrial count and an improved respiratory function in cultured cells (see Non-Patent Literature 5). Higher energy expenditure and resistance to obesity are observed in PGC-1β transgenic mice (see Non-Patent Literature 6).

PGC-1β is known to relate to control of, for example, determination and/or differentiation of brown fat, cellular metabolism, oxidation of fatty acids, and mitochondrial function and/or respiration (see Patent Document 1). PGC-1β is known to relate to control of lipogenesis and lipid transportation (see Patent Document 2).

CITATION LIST

Patent Literatures

Patent Literature 1: JP 2008-517931 A
Patent Literature 2: JP 2005-514921 A

Non Patent Literatures

Non-Patent Literature 1: Viana Abranches, et al. (2011). Peroxisome proliferator-activated receptor: effects on nutritional homeostasis, obesity and diabetes mellitus. Nutr Hosp 26, 271-279.
Non-Patent Literature 2: Andersson U. and Scarpulla R C., (2001) Pgc-1-related coactivator, a novel, serum-inducible coactivator of nuclear respiratory factor 1-dependent transcription in mammalian cells. Mol Cell Biol. 21, 3738-3749.
Non-Patent Literature 3: Kressler, D. et al., (2002). The PGC-1-related protein PERC is a selective coactivator of estrogen receptor alpha. J Biol Chem 277, 13918-13925.
Non-Patent Literature 4: Lin, J. (2001). Peroxisome Proliferator-activated Receptor gamma Coactivator 1beta (PGC-1beta), A Novel PGC-1-related Transcription Coactivator Associated with Host Cell Factor. J Biol Chem 277, 1645-1648.
Non-Patent Literature 5: St-Pierre, J., et al., (2003). Bioenergetic analysis of peroxisome proliferator-activated receptor gamma coactivators 1alpha and 1beta (PGC-1alpha and PGC-1beta) in muscle cells. J Biol Chem 278, 26597-26603.
Non-Patent Literature 6: Kamei, Y., et al., (2003). PPAR-gamma coactivator 1beta/ERR ligand 1 is an ERR protein ligand, whose expression induces a high-energy expenditure and antagonizes obesity. Proc Natl Acad Sci USA 100, 12378-12383.

SUMMARY OF INVENTION

Technical Problem

The PPAR coactivator 1 (PGC-1) β has various functions as mentioned above. A substance for increasing PGC-1β activity and a method for screening such a substance are desired.

An object of the present invention is to provide a substance for increasing PGC-1β activity and a screening method therefor.

An object of the present invention is to provide a mitochondria-function regulator which is effective in the prevention or treatment of obesity and a screening method therefor.

Solution to Problem

The inventors of the present invention finally found that gene clusters which involve β-oxidation and/or mitochondria biogenesis were markedly up-regulated in conditional knockout mice of synoviolin and the number of mitochondria was significantly increased in their white fat cells, and that coactivator PGC-1β which regulates transcription of the gene clusters is negatively regulated by synoviolin. The present invention has been completed based on the above-described knowledge.

The first aspect of the present invention relates to a PGC-1β-protein-function regulator (agent of the present invention). The PGC-1β-protein-function regulator contains, as an active ingredient, a synoviolin expression inhibitor or a synoviolin activity inhibitor. The PGC-1β-protein-function regulator facilitates β-oxidation of fatty acid and expression or activation of mitochondria, for example, by regulating PGC-1β protein so that activity of the PGC-1β protein is increased. Therefore, the PGC-1β-protein-function regulator of the present invention is effective for, for example, prevention or treatment of condition such as obesity to which the PGC-1β protein relates.

In other words, the agent of the present invention increases the activity of the PGC-1β protein by inhibiting the synoviolin, and thereby increases the activation of mitochondria. Accordingly, the agent of the present invention is beneficial to prevention or treatment of obesity.

A preferable embodiment of the PGC-1β-protein-function regulator relating to the first aspect of the present invention is used for one of or both of facilitation of β-oxidation of fatty acid by PGC-1β protein, and facilitation of expression or activation of mitochondria by PGC-1β protein.

Specifically, the PGC-1β-protein-function regulator of the present invention is preferably used for activation of mitochondria. Thus the present invention also provides a mitochondria activator. The mitochondria activator is, for example, used for causing one of or both of increase in expression level of mitochondria and increase in size of mitochondria.

The second aspect of the present invention relates to a screening method for PGC-1β-protein-function regulator. In the method, firstly, a test substance is administrated to adipose tissue cells or individual animals. After that, at least one of the followings in the adipose tissue cells is measured or detected: expression level of synoviolin; a bond between synoviolin and PGC-1β-protein; and a ubiquitination of PGC-1β-protein caused by synoviolin. As described above, the present invention is based on the findings that inhibiting the activation of synoviolin causes to increase the activation of PGC-1β protein. Measuring the expression or activity of the synoviolin enables screening the PGC-1β-protein-function regulator which is a substance having an action to regulate functions of the PGC-1β protein.

One embodiment of the second aspect of the present invention relates to a detecting (screening) method for a mitochondria activator using the above described screening method for the PGC-1β-protein-function regulator.

Another embodiment of the second aspect of the present invention relates to a detecting (screening) method for an anti-obesity therapeutic agent or an anti-obesity prevention agent using the above described screening method for the PGC-1β-protein-function regulator.

Advantageous Effects of Invention

The present invention provides, for example, a PGC-1β-protein-function regulator and a screening method therefor, and a mitochondria-function regulator effective for prevention or treatment of obesity and a screening method therefor.

BRIEF DESCRIPTION OF DRAWINGS

FIG. 11-1 shows results of Western blot (upper diagrams) showing binding inhibition effects between synoviolin and PGC-1β by test substances 349 and 348, and graphs showing evaluations of binding ability of the test substances 349 and 348 (lower diagrams).

FIG. 11-2 shows results of Western blot (upper diagrams) showing binding inhibition effects between synoviolin and PGC-1β by test substances quercetin and 351, and graphs showing evaluations of binding ability of the test substances quercetin and 351 (lower left and right diagrams).

FIG. 11-3 is a result of Western blot showing a binding inhibiting effect of each test substance.

FIG. 11-4 shows another result of Western blot showing a binding inhibition effect between synoviolin and PGC-1β by test substances. The degree of binding is graphed as intensity through an image analysis of results of Western blot in binding assay.

FIG. 20 is diagrams showing results of in vitro ubiquitination assay.

FIG. 21 is a result of Western blot showing a concentration dependence of ubiquitination inhibiting activity of PGC-1β by test substances 348 and 349.

FIG. 22 shows amino acid sequences of SyU domains in multiple species.

DESCRIPTION OF EMBODIMENTS

Figure 1:
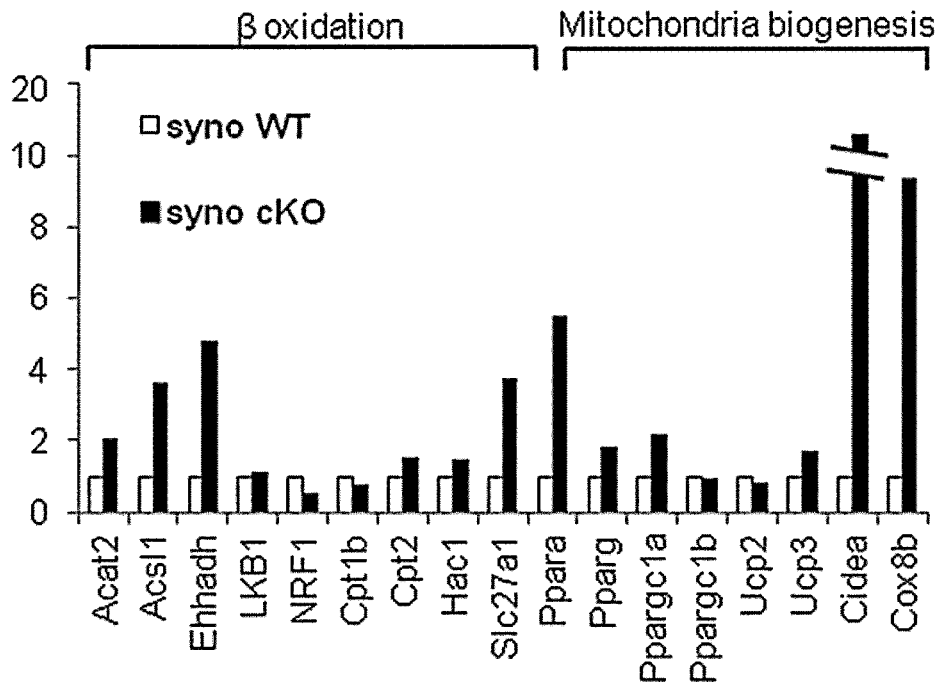
FIG. 1 is a graph showing β-oxidation in white fat cells from synoviolin knockout mice and a transcription level of mitochondrial related genes.

The first aspect of the present invention relates to a PGC-1β-protein-function regulator (agent of the present invention). PGC-1β means PPAR coactivator 1β. The PGC-1β-protein-function regulator is, for example, an agent for regulating various functions of the above described PGC-1β protein. The PGC-1β protein has various functions. Thus regulating the functions of the PGC-1β protein is beneficial to analysis of various biological functions to which the PGC-1β protein is involved.

The PGC-1β-protein-function regulator contains, as an active ingredient, a synoviolin expression inhibitor or a synoviolin activity inhibitor. The synoviolin expression inhibitor and the synoviolin activity inhibitor are publicly known. The synoviolin expression inhibitor or the synoviolin activity inhibitor may be obtained by obtaining candidate compounds by using the screening method described later and by measuring whether the candidate compounds have activity to inhibit expression of synoviolin or capacity to inhibit activity of synoviolin. The PGC-1β-protein-function regulator of the present invention facilitates β-oxidation of fatty acid and expression or activation of mitochondria by regulating PGC-1β protein so that activation of the PGC-1β protein is increased. Accordingly, the PGC-1β-protein-function regulator of the present invention is effective for, for example, prevention or treatment of condition such as obesity to which the PGC-1β protein is involved.

The accession number of human synoviolin gene in the public gene database Genbank is AB024690 (SEQ ID NO: 1).

The nucleotide sequence of the gene encoding human synoviolin is shown in SEQ ID NO: 1. Moreover, proteins other than the protein encoded by this nucleotide sequence, that are highly homologous to the sequence (normally, 70% or more; preferably 80% or more; more preferably 90% or more; and most preferably 95% or more) and have functions of the synoviolin protein, are included in the synoviolin of the present invention.

The term "synoviolin gene" as used herein includes, for example, endogenous genes of other organisms that correspond to a DNA comprising the nucleotide sequence of SEQ ID NO: 1 (such as that of homologs of the human synoviolin gene).

Moreover, the endogenous DNA of other organisms that corresponds to DNA comprising the nucleotide sequence of SEQ ID NO: 1 is generally highly homologous to the DNA of SEQ ID NO: 1. The term "highly homologous" means a homology of 50% or more, preferably 70% or more, more preferably 80% or more, and yet more preferably 90% or more (for example, 95% or more, and further, 96%, 97%, 98%, or 99% or more). This homology can be determined using the mBLAST algorithm (Altschul et al., 1990, Proc. Natl. Acad. Sci. USA 87: 2264-8; Karlin and Altschul, 1993, Proc. Natl. Acad. Sci. USA 90: 5873-7). Moreover, if the DNA is isolated from an organism, it is considered to hybridize with the DNA of SEQ ID NO: 1 under stringent conditions. Here, examples of the "stringent conditions" include "2×SSC, 0.1% SDS, 50° C.", "2×SSC, 0.1% SDS, 42° C.", and "1×SSC, 0.1% SDS, 37° C.". Examples of more stringent conditions include "2×SSC, 0.1% SDS, 65° C.", "0.5×SSC, 0.1% SDS, 42° C.", and "0.2×SSC, 0.1% SDS, 65° C.". Those skilled in the art are capable of appropriately obtaining endogenous genes of other organisms that correspond to the synoviolin gene, based on the nucleotide sequence of the synoviolin gene. In the present specification, proteins (genes) corresponding to synoviolin proteins (genes) in organisms other than humans, or proteins (genes) functionally equivalent to the synoviolin described above, may be simply referred to as "synoviolin protein (gene)".

The "synoviolin" of the present invention can be prepared as a natural protein or as a recombinant protein using gene recombination techniques. Natural proteins can be prepared, for example, by a method using affinity chromatography, which employs antibodies against synoviolin protein, from cell (tissue) extracts considered to express the synoviolin protein. In addition, recombinant proteins can be prepared by culturing cells transfected by DNA encoding the synoviolin protein. The "synoviolin protein" of the present invention is suitably used in, for example, the screening methods described below.

In the present invention, the term "expression" includes "transcription" from genes, "translation" into polypeptides, and the "inhibition of degradation" of proteins. The "expression of synoviolin protein" means the occurrence of the transcription and translation of a gene encoding the synoviolin protein, or the production of the synoviolin protein by such transcription and translation.

The various functions mentioned above can be appropriately evaluated (measured), using general techniques, by those skilled in the art. Specifically, the methods described in the Examples below, or such methods suitably modified, can be performed.

Accordingly, the term "synoviolin expression inhibitor or synoviolin activity inhibitor" refers to lowering or eliminating the quantity, function, or activity of a synoviolin gene or protein as compared with the quantity, function, or activity of the wild-type synoviolin gene or protein. The term "inhibition" includes the inhibition of either or both of function and expression.

Specifically, ubiquitination means a process for the formation of a polyubiquitin chain via repeated cascade of reactions with enzymes such as ubiquitin-activating enzyme (E1), ubiquitin-conjugating enzyme (E2), and ubiquitin ligase (E3), by which ubiquitin molecules are conjugated in a branched form to a substrate protein. The polyubiquitin chain is formed via an ε-amino group at Lys48 in ubiquitin molecules, and then becomes a degradation signal for the 26S proteasome, leading to the degradation of target proteins.

To confirm influences on synoviolin gene expression or synoviolin protein activity by test substances, such a method as disclosed in WO 2006-137514 can be used.

Influence of synoviolin protein on self-ubiquitination

For example, JP 2008-74753 A (Japanese Patent No. 5008932) discloses that plumbagin (2-methyl-5-hydroxy-1,4-naphthoquinone) and quercetin (2-(3,4-dihydroxyphenyl)-3,5,7-trihydroxy-4H-1-benzopyrano-4-on) inhibit self-ubiquitination of synoviolin protein. The self-ubiquitination of synoviolin means ubiquitination of protein caused by synoviolin-synoviolin interactions as disclosed in JP 2008-74753 A. The self-ubiquitination of protein occurs when synoviolin binds to protein.

Influence of synoviolin protein on self-ubiquitination may be confirmed by using a method disclosed in JP 2008-74753 A (Japanese Patent No. 5008932). For example, test substances may be added to in vitro self-ubiquitination reaction solution containing MBP-Syno ΔTM-His, and incubate at 37° C. for 30 minutes. After the incubation, Western blot analysis using anti-HA antibody may be performed to detect ubiquitinated protein. MBP-Syno ΔTM-His means synoviolin in which transmembrane domain has been deleted and which has maltose-binding protein fused to N terminus side thereof and His tag fused to C terminus side thereof.

Synoviolin Expression Inhibitor or Synoviolin Activity Inhibitor

Examples of synoviolin expression inhibitor or synoviolin activity inhibitor are plumbagin (2-methyl-5-hydroxy-1,4-naphthoquinone) and quercetin (2-(3,4-dihydroxyphenyl)-3,5,7-trihydroxy-4H-1-benzopyrano-4-on) which are disclosed in Japanese Patent No. 5008932, and its pharmacologically acceptable salt or their hydrate.

An example of synoviolin expression inhibitor or synoviolin activity inhibitor is a ubiquitination activity inhibitor of synoviolin protein containing naphthalene derivative of formula (I), pharmaceutically acceptable salts thereof, or pharmaceutically acceptable solvates thereof. Compounds expressed by the formula (I) can be compounded by known methods.

The ubiquitination activity inhibitor of synoviolin protein means an agent to inhibit self-ubiquitination activity of synoviolin. As disclosed later in example, whether the ubiquitination activity is inhibited can be evaluated by, for example, measuring an amount of protein ubiquitinated in vitro. As described later, the ubiquitination activity inhibitor of synoviolin protein is effective as, for example, an obesity therapeutic or prevention agent as well as a rheumatism therapeutic or prevention agent.

The pharmaceutically acceptable salts thereof mean pharmaceutically acceptable salts of naphthalene derivative of formula (I). The pharmaceutically acceptable solvates thereof mean pharmaceutically acceptable solvates of naphthalene derivative of formula (I). Examples of the pharmaceutically acceptable salts include inorganic acid salts, organic acid salts, inorganic basic salts, organic basic salts, and acidic or basic amino acid salts. Examples of the inorganic acid salts include hydrochlorides, hydrobromides, sulfates, nitrates, and phosphates. Examples of the organic acid salts include acetates, succinates, fumarates, maleates, tartrates, citrates, lactates, stearates, benzoates, methanesulfonates, and p-toluenesulfonates. Examples of the inorganic basic salts include alkali metal salts such as sodium salts and potassium salts, alkaline earth metal salts such as calcium salts and magnesium salts, aluminum salts, and ammonium salts. Examples of the organic basic salts include diethylamine salts, diethanolamine salts, meglumine salts, and N,N'-dibenzylethylenediamine salts. Examples of the acidic amino acid salts include aspartates and glutamates. Examples of the basic amino acid salts include arginine salts, lysine salts, and ornithine salts. Examples of solvates include hydrates.

The compounds of the present invention can be isolated/purified by using known methods while applying conventional chemical procedures such as extraction, concentration, evaporation, crystallization, filtration, recrystallization, and various forms of chromatography.

[Chemical Formula 1]

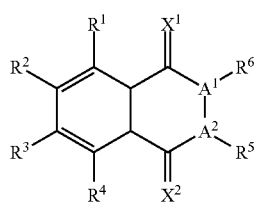

(I)

In the formula (I), $R^1$ to $R^4$ may be the same or different, and each represents one of a hydrogen atom, a hydroxyl group, a $C_{1-3}$ alkyl group, a $C_{1-3}$ alkoxy group, and a halogen atom. As demonstrated by the examples described below, at least one of $R^1$ to $R^4$ is the hydroxyl group.

$R^5$ and $R^6$ may be the same or different, and each represents one of a hydrogen atom, a $C_{1-3}$ alkyl group, and a halogen atom.

$X^1$ and $X^2$ may be the same or different, and each represents an oxygen atom or a sulfur atom.

$A^1$-$A^2$ represents a C—C (single bond) or a C=C (double bond). In a case that the $A^1$-$A^2$ is the C=C (double bond), the formula (I) is represented by the formula (II).

The $C_{1-3}$ alkyl group means an alkyl group having 1 to 3 carbon atoms. Examples of the $C_{1-3}$ alkyl group area methyl group, an ethyl group, a n-propyl group, and an isopropyl group. A preferred example of the $C_{1-3}$ alkyl group is a methyl group.

The $C_{1-3}$ alkoxy group means alkoxy group having 1 to 3 carbon atoms. Examples of the $C_{1-3}$ alkoxy group are a methoxy group, an ethoxy group, a n-propoxy group, and an isopropoxy group. A preferred example of the $C_{1-3}$ alkoxy group is a methoxy group.

Examples of the halogen atom are a fluorine atom, a chlorine atom, a bromine atom, and an iodine atom. A preferred example of the halogen atom is a chlorine atom.

A preferred embodiment of the present invention relates to a ubiquitination activity inhibitor of synoviolin protein in which at least one of $R^1$ and $R^4$ is the hydroxyl group.

A preferred embodiment of the present invention is ubiquitination activity inhibitor of synoviolin protein, wherein $A^1$-$A^2$ represents C=C in the general formula (I). The naphthalene derivative is a naphthalene derivative represented by the following formula (II).

[Chemical Formula 2]

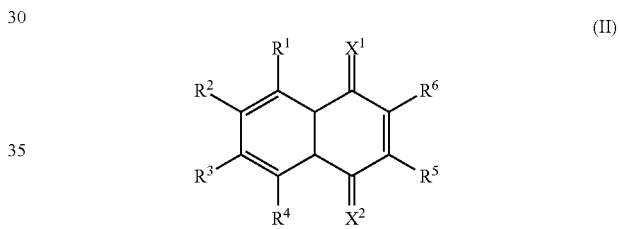

(II)

A preferred embodiment of the present invention is a ubiquitination activity inhibitor of synoviolin protein, wherein each $X^1$ and $X^2$ represents an oxygen atom and $A^1$-$A^2$ represents C=C in the formula (I). The naphthalene derivative is a naphthoquinone derivative represented by the following formula (III).

[Chemical Formula 3]

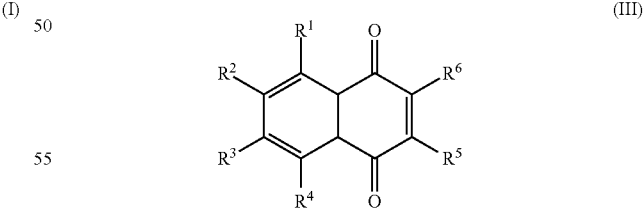

(III)

A preferred embodiment of the present invention is a ubiquitination activity inhibitor of synoviolin protein, wherein in the formula (I), $R^1$ to $R^4$ may be the same or different, and each represents one of a hydrogen atom, a hydroxyl group, a methyl group, a methoxy group, and a chlorine atom, where at least one of $R^1$ to $R^4$ is a hydroxyl group, $R^5$ and $R^6$ may be the same or different, and each represents a hydrogen atom or a methyl group, each of $X^1$ and $X^2$ represents an oxygen atom, and
$A^1$-$A^2$ represents C=C.

A preferred embodiment of the present invention is a ubiquitination activity inhibitor of synoviolin protein, wherein in the formula (I), $R^1$ to $R^4$ may be the same or different, and each represents one of a hydrogen atom, a hydroxyl group, a methyl group, a methoxy group, and a chlorine atom, where at least one of $R^1$ to $R^4$ is the hydroxyl group, $R^2$ and $R^3$ represent the hydrogen atoms,
each of $R^5$ and $R^6$ represents a hydrogen atom,
each of $X^1$ and $X^2$ represents an oxygen atom, and
$A^1$-$A^2$ represents C=C.

A preferred embodiment of the present invention is a ubiquitination activity inhibitor of synoviolin protein, wherein the naphthalene derivative represented by the formula (I) is one of or two or more of
5,8-dihydroxy-4a,8a-dihydro-[1,4]naphthoquinone,
5-hydroxy-4a,8a-dihydro-[1,4]naphthoquinone, 5-hydroxy-2,3,4a,8a-tetrahydro-[1,4]naphthoquinone, 5-hydroxy-7-methoxy-4a,8a-dihydro-[1,4]naphathoquinone, 5-hydroxy-8-methoxy-4a,8a-dihydro-[1,4]naphthoquinone, and
5-chloro-8-hydroxy-4a,8 dihydro-[1,4]naphthoquinone.

An embodiment of the synoviolin expression inhibitor or the synoviolin activity inhibitor contains siRNA of synoviolin as an active ingredient. Nucleic acids having an inhibitory action by means of the RNAi effect are generally referred to as siRNA or shRNA. RNAi is a phenomenon in which, when a short double-stranded RNA (herein abbreviated as "dsRNA") that is composed of a sense RNA comprising a sequence homologous to mRNA of the target gene, and an antisense RNA comprising the complementary sequence thereto, is introduced into a cell, the dsRNA specifically and selectively binds to target gene mRNA and induces its disruption, and efficiently inhibits (suppresses) target gene expression by cleaving the target gene. For example, when dsRNA is introduced into a cell, the expression of a gene having a sequence homologous to the RNA is suppressed (knocked down). As RNAi is capable of suppressing target gene expression as described above, the technique is attracting attention as a simple gene knockout method replacing conventional gene disruption methods based on homologous recombination, which is complicated and inefficient, and as a method applicable to gene therapy. RNA used for RNAi is not necessarily completely identical to the synoviolin gene or to a partial region of the gene, although it is preferably completely homologous.

siRNA can be designed as follows:
(a) There is no specific limitation to a target region, and any region in the gene encoding synoviolin can be used as a target candidate. For example, in the case of humans, any region described in GenBank accession No. AB024690 (SEQ ID NO: 1) can be used as a candidate.
(b) Among selected regions, sequences which start with AA and have 19 to 25 bases long, preferably 19 to 21 bases long, are selected. For example, sequences having a CG content of 40 to 60% may be selected.
(a) contacting a test compound with a cell expressing the synoviolin gene;
(b) measuring synoviolin gene expression in the cell; and
(c) selecting a compound lowering the expression level as compared to that measured in the absence of the test compound.

An example of synoviolin siRNA is RNA having sequence selected from the following SEQ ID Nos. 2 to 6, complemental sequences thereof, or sequence obtained by replacing, inserting, deleting, or adding one base or two bases with respect to one of these sequences. The RNA having sequences represented by the SEQ ID Nos. 2 to 4 are known as synoviolin siRNA as disclosed in Izumi T, et al., Arthritis Rheum. 2009; 60(1); 63-72., EMBO, Yamasaki S, et al., EMBO J. 2007; 26(1): 113-22. by using experiments. The RNA having sequences represented by the SEQ ID Nos. 5 and 6 are known as synoviolin siRNA as disclosed in WO 2005/074988 by using experiments.

```
SEQ ID No. 2:      5'-GCUGUGACAGAUGCCAUCA-3'
SEQ ID No. 3:      5'-GGUGUUCUUUGGGCAACUG-3'
SEQ ID No. 4:      5'-GGUUCUGCUGUACAUGGCC-3'
SEQ ID No. 5:      5'-CGUUCCUGGUACGCCGUCA-3'
SEQ ID No. 6:      5'-GUUUTGGUGACUGGUGCUA-3'
```

The "RNA having a sequence obtained by replacing, inserting, deleting, or adding one base or two bases with respect to one of these sequences" is RNA having a sequence obtained by replacing, inserting, deleting, or adding one base or two bases with respect to the sequence selected from the SEQ ID Nos. 2 to 6 or the complemental sequences thereof. One of replacement, insertion, deletion, and addition may be occurred, and two or more may be occurred.

For example, WO 2005-018675 and WO 2005-074988 disclose siRNA to a gene encoding synoviolin, screening method thereof, and evaluation method thereof. In the present invention, siRNA to a gene encoding synoviolin can be evaluated by appropriately using the methods disclosed in these publications.

An embodiment of the synoviolin expression inhibitor or the synoviolin activity inhibitor contains, as an active ingredient, a synoviolin decoy nucleic acid having asequence represented by SEQ ID No. 7 or a sequence obtained by replacing, inserting, deleting, or adding one base or two bases with respect to the sequence represented by SEQ ID No. 7. The nucleic acid having the sequence represented by the SEQ ID No. 7 is known as synoviolin decoy nucleic acid as disclosed in Tsuchimochi K, et al., Mol Cell Biol. 2005; 25(16): 7344-56 by examples (SEQ ID No. 7: 5'-AUG-GUGACUGGUGCUAAGA-3').

The synoviolin decoy nucleic acid and a confirmation method thereof are known as disclosed in, for example, WO 2005-093067 and WO 2005-074988.

Another embodiment of the synoviolin expression inhibitor or the synoviolin activity inhibitor contains, as an active ingredient, a synoviolin antisense nucleic acid. The synoviolin antisense nucleic acid and a screening method thereof are disclosed in, for example, JP 2009-155204 A, JP 2006-137514 A1, and JP 2005-074988 A1. The synoviolin antisense nucleic acid means a nucleic acid which has complemental sequence of synoviolin gene and hybridizes with the gene to inhibit synoviolin gene expression. The antisense nucleic acid can be prepared by synthesizing nucleic acid compounds complementary to partial sequence of a gene encoding synoviolin using synthetic chemical technique. In order to confirm whether the nucleic acid compounds efficiently inhibit synoviolin production, screening test may be performed using the expression level of the gene as an index. An example of the antisense nucleic acid compound is the one that can suppress synoviolin expression at least to 50% or less as compared with control.

To inhibit the expression of a specific endogenous gene, methods using antisense technology are well known to those skilled in the art. There are multiple factors by which an antisense nucleic acid inhibits target gene expression. These include inhibition of transcription initiation by triple strand formation, transcription inhibition by hybrid formation at a local open loop structure formed by RNA polymerase, transcription inhibition by hybrid formation with RNA being synthesized, splicing inhibition by hybrid formation at the junction between an intron and an exon, splicing inhibition by hybrid formation at a spliceosome formation site, inhibition of mRNA translocation from the nucleus to the cytoplasm by hybrid formation with mRNA, splicing inhibition by hybrid formation at a capping site or poly-A addition site, inhibition of translation initiation by hybrid formation at a translation initiation factor-binding site, translation inhibition by hybrid formation at a ribosome binding site near the initiation codon, inhibition of peptide chain elongation by hybrid formation in the translated region or polysome binding site of mRNA, inhibition of gene expression by hybrid formation at a nucleic acid-protein interaction site, etc. As described above, antisense nucleic acids inhibit target gene expression by interfering with various processes such as transcription, splicing, or translation (Hirashima and Inoue, "Shin Seikagaku Jikken Koza" [New Biochemistry Experimentation Lectures] 2; Kakusan (Nucleic Acids) IV; Idenshi No Fukusei To Hatsugen [Replication and Expression of Genes]" Edited by The Japanese Biochemical Society, Tokyo Kagaku Dozin, 319-347, 1993).

The antisense nucleic acids used in the present invention may inhibit synoviolin gene expression and/or function by any of the above mechanisms. In one embodiment, an antisense sequence designed to be complementary to the untranslated region near the 5'-terminal of mRNA of the synoviolin gene is considered to be effective in inhibiting the translation of the gene. Moreover, sequences complementary to the coding region or to the untranslated region on the 3' side can also be used. Thus, nucleic acids comprising not only antisense sequences of translated regions of the synoviolin gene, but also those of untranslated regions, are included in the antisense nucleic acids used in the present invention. The antisense nucleic acid to be used is linked to the downstream region of an appropriate promoter, and preferably, a sequence containing a transcription termination signal is connected to the 3' side. A desired animal (cell) can be transformed with the nucleic acid thus prepared using known methods. The sequence of the antisense nucleic acid is preferably complementary to the endogenous-synoviolin gene of the animal (cell) to be transformed or a portion thereof, but the sequence may not be completely complementary as long as the sequence can effectively inhibit gene expression. The transcribed RNA preferably has a complementarity of 90% or more, and most preferably 95% or more, to the transcript of the target gene. In order to effectively inhibit the expression of the target gene (synoviolin) using an antisense nucleic acid, the antisense nucleic acid is preferably at least 15 bases long but less than 25 bases long. However, antisense nucleic acids of the present invention are not necessarily limited to this length, and may be 100 bases long or longer, or 500 bases long or longer.

Moreover, ribozymes or DNAs encoding ribozymes can also be used to inhibit synoviolin gene expression. "Ribozyme" refers to RNA molecule that has a catalytic activity. Ribozymes having various kinds of activity are known. Studies focusing on ribozymes as RNA cleaving enzymes have made it possible to design ribozymes that site-specifically cleave RNA. Some ribozymes such as group I intron ribozymes or the M1 RNA contained in RNase P consist of 400 nucleotides or more, whereas others, called the hammerhead or hairpin ribozymes, have an activation domain of about 40 nucleotides (M. Koizumi and E. Ohtsuka, Tanpakushitsu Kakusan Kohso [Protein, Nucleic Acid, and Enzyme], 35: 2191, 1990).

For example, the self-cleavage domain of hammerhead ribozymes cleaves the 3' side of C15 in the G13U14C15 sequence. The base pair formation between U14 and A9 is considered important for the above cleavage activity, and it has been shown that the cleavage may also occur when C15 is replaced with A15 or U15 (M. Koizumi et al., FEBS Lett. 228: 228, 1988). When ribozymes are designed to have substrate-binding sites that are complementary to RNA sequences near target sites, they can be restriction enzyme-like RNA-cleaving ribozymes that recognize the sequence of UC, UU, or UA in target RNA (Koizumi, M. et al., FEBS Lett. 239: 285, 1988; M. Koizumi and E. Ohtsuka, Tanpakushitsu Kakusan Kohso [Protein, Nucleic acid, and Enzyme], 35: 2191, 1990; Koizumi, M. et al., Nucl. Acids Res. 17: 7059, 1989).

Hairpin type ribozymes are also useful for the purpose of the present invention. Such ribozyme can be found, for example, in the minus strand of the satellite RNA of tobacco ringspot virus (Buzayan, J. M., Nature, 323: 349, 1986). It has been disclosed that target-specific RNA-cleaving ribozymes can also be designed from hairpin type ribozymes (Kikuchi, Y. and Sasaki, N., Nucleic Acids Res. 19: 6751, 1991; Yo Kikuchi, Kagaku To Seibutsu [Chemistry and Biology] 30: 112, 1992). Thus, the expression of the synoviolin gene of the present invention can be inhibited by specifically cleaving the transcript of the gene.

The expression of endogenous genes can also be suppressed by RNA interference (hereinafter abbreviated as "RNAi") using a double-stranded RNA having the same or similar sequence to the target gene sequence.

The therapeutic agent of the present invention can be administered orally or parenterally. Examples of parenteral administration type therapeutic agent of the present invention include transpulmonary administration agent type (e.g. using nebulizer etc.), transnasal administration agent type, transdermal administration agent type (e.g. ointment, creams), injection type, and the like. The injection type therapeutic agent can be administered to the whole body or locally by intravenous injection such as dripping, intramuscular injection, intraperitoneal injection, hypodermic injection, or the like.

Administration method is appropriately selected depending on age and symptom of a patient. Effective administration amount is 0.1 µg to 100 mg, preferably 1 µg to 10 µg per 1 kg body weight for one administration. However, administration amount of the above therapeutic agent is not restricted to these administration amounts. In a case that nucleic acid such as siRNA is mixed, an amount of the nucleic acid is, for example, 0.01 to 10 µg/ml, preferably 0.1 to 1 µg/ml.

The therapeutic agent of the present invention can be formulated in the usual manner and may contain pharmaceutically acceptable carriers or additives. Such carriers or additives include water, pharmaceutically acceptable organic solvents, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerine, glycerol, propylene glycol, vaseline, paraffin, stearyl alcohol, stearic acid, human serum albumin, mannitol, sorbitol, lactose, surfactant acceptable as pharmaceutical additive, and the like.

The above additive may be selected alone or appropriately in combination from the above additives depending on the pharmaceutical form of the therapeutic agent of the present invention. For example, in a case of being used as an injectable preparation, refined ER stress inducer may be dissolved into a solvent (e.g. saline, buffer solution, glucose solution, or the like), and Tween80, Tween20, gelatin, human serum albumin, or the like may be added to the solution. Alternatively, the therapeutic agent of the present invention may be lyophilized to have a pharmaceutical form of dissolving before use. For example, sugar alcohol or saccharide such as mannitol or glucose can be used as excipient for lyophilization.

The second aspect of the present invention relates to a screening method for PGC-1β-protein-function regulator. It is preferable to improve function of PGC-1β protein. It is preferable for the regulator which improves function of PGC-1β protein to act on anti-obesity. In this method, test substances are applied to cells in adipose tissue or to animal individual. After that, at least one of expression level of synoviolin in the cells of the adipose tissue, binding between synoviolin and PGC-1β protein, and ubiquitination of PGC-1β protein by synoviolin is measured or detected. As described above, the present invention is based on the knowledge that inhibiting the activity of the synoviolin causes to increase the activity of PGC-1β protein. Measuring the expression or activity of the synoviolin enables screening the PGC-1β-protein-function regulator (a substance having an action to regulate functions of the PGC-1β protein). Namely, the screening method for PGC-1β-protein-function regulator may include screening for a substance which inhibits expression or activity of synoviolin. Methods disclosed in, for example, JP. 2006/137514 A1, JP 2006/135109 A1, JP 2005/118841 A1, JP 2005/019472 A1, and JP 02/052007 A1 as well as the methods described in the specification and the examples of this application may be appropriately applied to the screening method for the substance which inhibits expression or functions of synoviolin.

One embodiment of the second aspect of the present invention relates to a detecting (screening) method for a mitochondria activator using the above described screening method for the PGC-1β-protein-function regulator.

Another embodiment of the second aspect of the present invention relates to a detecting (screening) method for an anti-obesity therapeutic agent or an anti-obesity prevention agent using the above described screening method for the PGC-1β-protein-function regulator.

EXAMPLES

Hereinafter, the present invention is further specifically described using Examples. The present invention is not limited to the examples described below.

(Materials: Plasmids and Antibodies)

The coding sequences for full-length mPPARα, mPPARγ, mPGC-1α and mPGC-1β genes were obtained by PCR amplification from mouse 3T3-L1 cDNA. Fragments of a series of deletion mutants of PGC-1β were obtained by PCR amplification. Full-length PGC-1β and each of these deletion mutants were inserted into pcDNA3 HA vector (this vector was prepared by modification of a vector purchased from Amersham Pharmacia Biotech), and used for the GST pull-down assay and transient transfection assay. The sequences of all prepared plasmids were confirmed by sequence analysis. PPREx3-TK-luc was purchased from addgene Inc. A series of synoviolin plasmids were used those previously disclosed in the literatures (Amano et al., 2003. Synoviolin/Hrd1, an E3 ubiquitin ligase, as a novel pathogenic factor for arthropathy. Genes Dev 17, 2436-2449) (Yamasaki et al., 2007. Cytoplasmic destruction of p53 by the endoplasmic reticulum-resident ubiquitin ligase 'Synoviolin'. EMBO J 26, 113-122.). The following antibodies were used: anti-FLAG (M2), anti-tubulin from Sigma Chemical Co, anti-HA-tag (12CA5 and 3F10) from Roche, and anti-PGC-1β from Sant cruze bio. Anti-synoviolin rabbit polyclonal antibody described previously (Yamasaki et al., 2007) was used.

Generation Example 1: Synoviolin Conditional Knockout Mice

Synoviolin conditional knockout mice (syno cKO) were prepared using the following method.

14.8 kb gene region, the region from upstream of exon 1 to downstream of exon 16 of mouse synoviolin gene, was used to construct the targeting vector. A neomycin resistance gene interposed between FRT sequences was inserted between exon 1 and exon 2. In addition, loxP sequences were introduced upstream from exon 2 and downstream from exon 14. The resulting targeting vector was introduced into ES cells. Clones having an allele in which the desired homologous recombination has occurred were selected by confirming removal of the loxP-exon-loxP sequence by Cre treatment and removal of the FRT-neomycin-FRT sequence by FLP treatment using the lengths of the PCR products. Chimeric mice were obtained by introducing the ES cell clones that had the desired homologous recombination into mouse embryos as described in a known method (e.g., EMBO J 16: 1850-1857). Moreover, these chimeric mice were crossed with wild-type C57BL/6 mice to generate mice in which the neomycin sequence had been removed. In addition, since loxP sequences between exons and the long arm incorporated in the targeting vector have the possibility of being lost during homologous recombination, their presence was confirmed by PCR.

The resulting neomycin-removed mice were crossed with CAG-Cre mice to obtain CAG-Cre;syno$^{flox/flox}$ mice having homozygous synoviolin allele in which loxP sequences were introduced and homozygous Cre-ER introduced gene under control of CMV enhancer and chicken β-actin promoter (See Hayashi, S., and McMahon, A. P. (2002). Efficient recombination in diverse tissues by a tamoxifen-inducible form of Cre: a tool for temporally regulated gene activation/inactivation in the mouse. Dev. Biol. 244, 305-318.).

The mice can induce synoviolin knockout by tamoxifen (Tam).

At 7-8 weeks after birth, CAG-Cre;syno$^{flox/flox}$ mice (syno cKO) and homozygous syno$^{flox/flox}$ mice (syno WT) were administered with tamoxifen. Tamoxifen solution was prepared so that 20 mg/ml of tamoxifen to be administered had been dissolved in corn oil (WAKO). Administration of 125 mg/kg of the tamoxifen solution per day was performed by intraperitoneal for 5 consecutive days.

Knockout of synoviolin by administration of tamoxifen was confirmed by PCR of synoviolin on genome, detection of synoviolin mRNA using real-time PCR, Western blotting of synoviolin protein, and the like.

Example 1: Transcription of Factors Relating to β-Oxidation and Mitochondrial Biogenesis In order to examine possibility of synoviolin to change peripheral energy consumption, comprehensive gene expression analysis was performed by using microarray in white fat cells derived from synoviolin knockout mice.

The results show remarkable increases in expression of genes relating to the β-oxidation such as Ppara, Cpt1b, Cpt, Acox2, Ehhadh, Acsl1, Acat2 and in expression of genes relating to the mitochondrial biogenesis such as Pgc-1a, UCP3, cidea, cox8b, in the synoviolin knockout mice as compared to the synoviolin WT mice.

Accordingly, expression of these genes was confirmed using real-time PCR. Concretely, total RNA was extracted in the usual manner from white fat cells derived from the synoviolin knockout mice (syno cKO), and then real-time PCR was performed. Various primers shown in the following table 1 were used for real-time PCR.

TABLE 1

| Gene | Primer | SEQ ID No | Probe No |
|------|--------|-----------|----------|
| Ehhadh | F ccggtcaatgccatcagt | 8 | 109 |
|  | R ctaaccgtatggtccaaactagc | 9 |  |
| Acsl1 | F ctacggacagaccgagtgc | 10 | 27 |
|  | R tttacataattgcaaggcatgg | 11 |  |
| Acat2 | F actgtcaccccagcgaac | 12 | 89 |
|  | R ccaggagactattcttgctaaagg | 13 |  |
| Acox2 | F agattgggcctataggaaga | 14 | 26 |
|  | R caccgggaggtaccaagaa | 15 |  |
| Cpt1b | F cccaaaacagtatcccaatcat | 16 | 10 |
|  | R taagagacccgtagccatc | 17 |  |
| Cpt2 | F ccaaagaagcagcgatgg | 18 | 71 |
|  | R tagagctcaggcagggtga | 19 |  |
| Slc27a1 | F gacaagctggatcaggcaag | 20 | 1 |
|  | R gaggccacagaggctgttc | 21 |  |
| Hacl1 | F tccaggcgaacgtgactt | 22 | 10 |
|  | R cagaggtttctgccatgcta | 23 |  |
| Ucp1 | F accttcccgctggacact | 24 | 9 |
|  | R ggcaatccttctgttttttgc | 25 |  |
| Ucp2 | F agcctgagacctcaaagcag | 26 | 6 |
|  | R ccttcaatcggcaagacg | 27 |  |
| Ucp3 | F tacccaaccttggctagacg | 28 | 69 |
|  | R gtccgaggagagagcttgc | 29 |  |
| Ppara | F ccgagggctctgtcatca | 30 | 78 |
|  | R gggcagctgactgaggaa | 31 |  |
| Pparg | F ggaaagacaacggacaaatca | 32 | 68 |
|  | R attcggatggccacctct | 33 |  |
| Ppargc1a | F tgtggaactctctggaactgc | 34 | 63 |
|  | R agggttatcttggttggcttta | 35 |  |
| Ppargc1b | F ctccagttccggctcctc | 36 | 17 |
|  | R ccctctgctctcacgtctg | 37 |  |
| Cidea | F aaaccatgaccgaagtagcc | 38 | 66 |
|  | R aggccagttgtgatgactaagac | 39 |  |
| Cox8b | F ccagccaaaactcccactt | 40 | 102 |
|  | R gaaccatgaagccaacgac | 41 |  |
| LKB1 | F ggacgtgctgtacaatgagg | 42 |  |
|  | R gcatgccacatacgcagt | 43 |  |

TABLE 1-continued

| Gene | Primer | SEQ ID No | Probe No |
|------|--------|-----------|----------|
| NRF1 | F tggagtccaagatgctaatgg | 44 |  |
|  | R gcgaggctggttaccaca | 45 |  |

F: forward, R: reverse

As a control, real-time PCR was similarly performed using white fat cells derived from synoviolin wild type mice (syno WT).

Reaction condition of real-time PCR is shown below.
Stage 1 (Activation of polymerase): at 95° C. for 10 min
Stage 2 (Thermal denaturation): at 95° C. for 1 sec
(Annealing/Elongation): at 60° C. for 20 sec
Stage 3: repeating Stage 2 40 cycles Step One Plus (Applied Biosystems) was used as a real-time PCR apparatus.

Measured values were normalized using values in 18s ribosomal RNA as endogenous control, and were shown by the ratio to a mean value (n=3) of the syno WT. The results were shown in FIG. 1.

FIG. 1 shows increase in transcription of gene clusters relating to β-oxidation and mitochondrial biogenesis. Accordingly, the results indicate that mitochondria in the white fat cells are a target for the synoviolin knockout mice.

Example 2: Observation of Mitochondria in Synoviolin Knockout Mice

In the white fat cells derived from the synoviolin knockout mice (syno cKO) used in Example 1, mitochondria were observed in the usual manner by using an electron microscope. As a control, the white fat cells derived from synoviolin wild type mice (syno WT) were similarly observed. The results were shown in the left of FIG. 2.

Further, the white fat cells derived from mice in which synoviolin had been knocked out specifically in fat cells (syno Adipose KO) were similarly observed. The results were shown in the right of FIG. 2. The synoviolin knockout mice in which synoviolin had been knocked out specifically in fat cells were generated as follows. Firstly, Syvn1$^{flox/flox}$ mice were crossed with fatty acid-binding protein 4 (aP2)-Cre mice (Jackson Immunoresearch Laboratories) to acquire compound heterozygote including aP2-Cre-ER;Syvn1$^{flox/+}$ mice and the like. Secondly, aP2-Cre;Syvn1$^{flox/+}$ mice were crossed with Syvn1$^{flox/flox}$ mice as the second mating to acquire aP2-Cre;Syvn1$^{flox/flox}$ mice. Mice having genotype of Syvn1$^{flox/flox}$ and being deficient in Cre transgene were used as a control.

FIGS. 2A and 2B show that the number of mitochondria in the white fat cells derived from the synoviolin knockout mice was markedly increased as compared to those derived from the synoviolin wild type mice. Furthermore, the size of mitochondria was also markedly increased.

Example 3: Binding Between Synoviolin and PGC-1β In Vitro

Transcription factor family PPAR (PPARα, PPARγ) deeply relating to differentiation and activity of adipocytes, and corresponding transcription coactivator PGC family (PGC-1α, PGC-1β, PRC) were hitherto known as a factor having activity of controlling both β-oxidation and duplication of mitochondria. Accordingly, whether each factor described above can bind with synoviolin protein was confirmed.

Firstly, GST fusion synoviolin which lack transmembrane domain (GST syno ΔTM) was incubated with glutathione-Sepharose 4B. The GST fusion protein was incubated with whole cell extract from HEK-293T expressing HA PPARγ, HA PPARα, HA PGC-1α, or HA PGC-1β. Bound protein was eluted and separated by SDS-PAGE, and Western blot was performed using anti-HA antibody. GST which was not fused to any protein was used as a control. The results were shown in FIG. 3.

Figure 3:
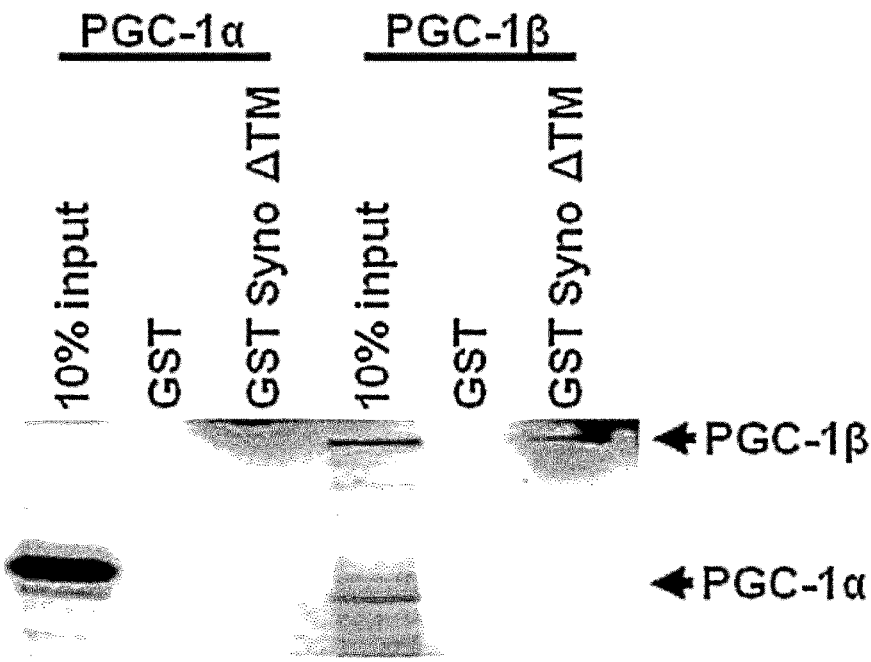
FIG. 3 is a result of Western blot showing binding between PGC-1β and synoviolin in vitro.

FIG. 3 shows that the GST used as a control did not bind to any proteins. On the other hand, GST syno ΔTM bound to HA PGC-1β and did not bind to each of HA PGC-1α, HA PPARγ, and HA PPARα. Accordingly, it was indicated that PGC-1β selectively binds to synoviolin protein.

Example 4: Binding Between Synoviolin and the Fragmented and Modified PGC-1β In Vitro In order to identify the binding region of PGC-1β which binds to synoviolin, GST pulldown assay was performed using a series of the fragmented and modified PGC-1β (See FIG. 4).

Specifically, the fragmentation of PGC-1β was performed by PCR according to a method in a previously reported article (Aratani, S. et al., (2001). Dual roles of RNA helicase A in CREB-department transcription. Mol. Cell Biol. 21, 4460-4469.). Conceptual diagrams of each fragmented and modified PGC-1β were shown in FIG. 4. In vitro binding assay was performed using the fragmented and modified PGC-1β with HA tag, which were transcribed/translated in vitro, and GST or GST-synoviolin ΔTM. These proteins were eluted and separated by SDS-PAGE, and Western blot was performed using anti-HA antibody. The results were shown in FIG. 4.

Figure 4:
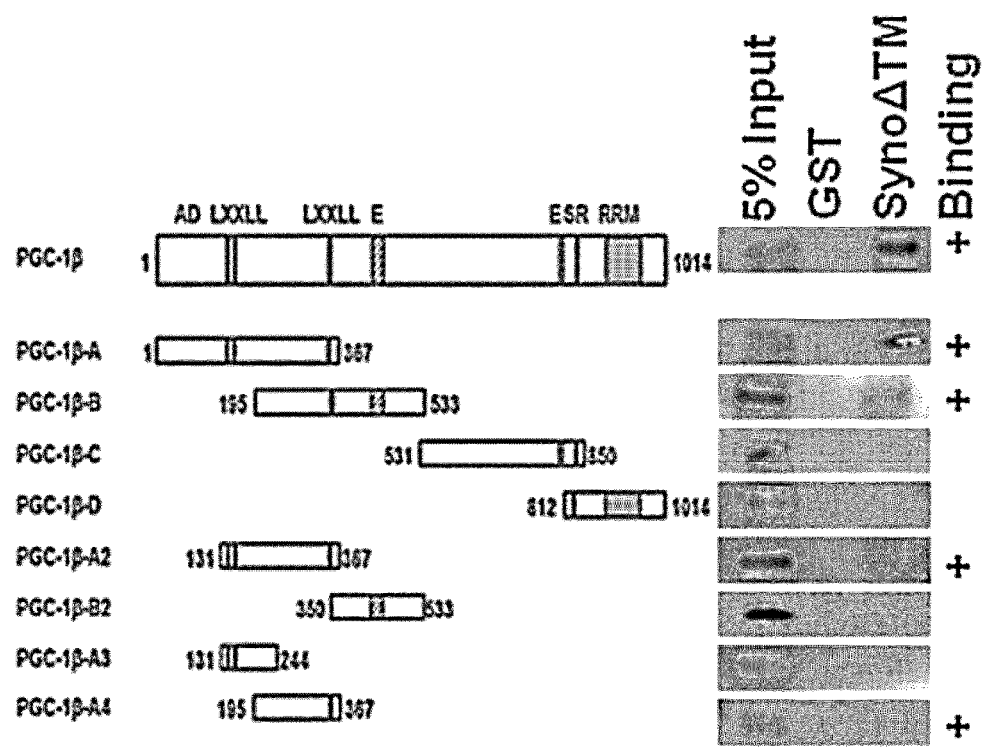
FIG. 4 is a conceptual diagram illustrating PGC-1β and fragmented PGC-1β, and a result of Western blot showing binding between the fragmented PGC-1β and synoviolin in vitro. Abbreviations in FIG. 4 are described below. AD: activation domain, LXXLL: LXXLL motif, E: glutamic acid-rich domain, SR: serine-arginine-rich domain, RRM: RNA recognition motif.

FIG. 4 shows that synoviolin bound to PGC-1β region (195 to 367 amino acid region) having a LXXLL motif which is unique in PGC-1β. With respect to the 195 to 367 amino acid region of PGC-1β, neither PGC-1α nor PRC includes the unique sequence.

Example 5: Binding Between Fragmented and the Modified Synoviolin and PGC-1β In Vitro In order to identify a region of synoviolin which binds to PGC-1β, GST pulldown assay was performed using a series of the fragmented and modified synoviolin (See FIG. 5 and already reported article of Yamasaki et al., 2007). HA PGC-1β generated by In vitro transcription/translation was incubated with GST or the fragmented and modified synoviolin fused to GST in a manner similar to Example 4, and Western blot was performed using anti-HA antibody. The results were shown in FIG. 5.

Figure 5:
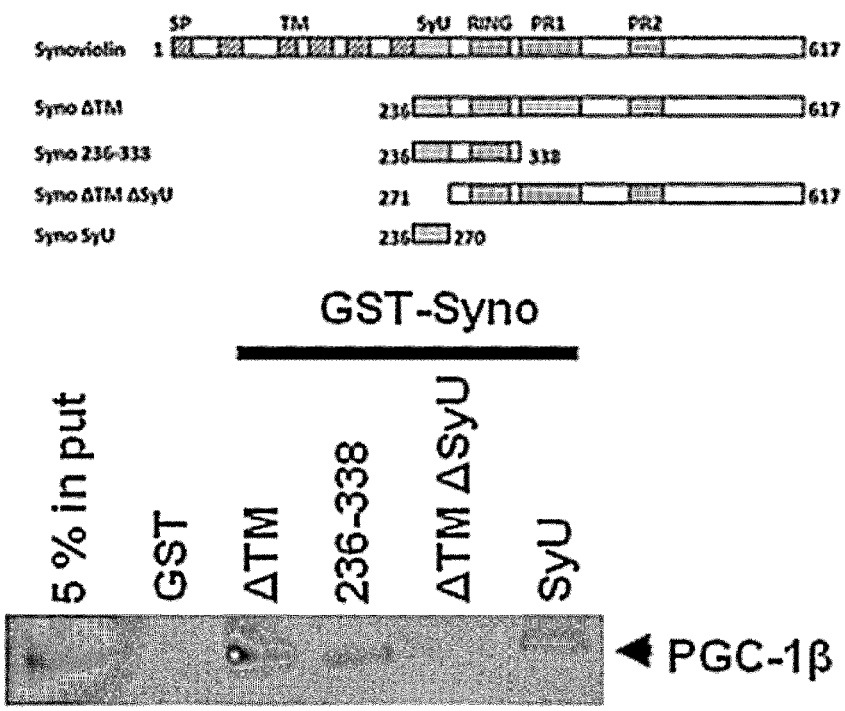
FIG. 5 is a conceptual diagram illustrating synoviolin and fragmented synoviolin, and a result of Western blot showing binding between PGC-1β and the fragmented synoviolin in vitro. Abbreviations in FIG. 4 are described below. SP: signal peptide, TM: transmembrane domain, SyU: unique domain to synoviolin, RING: RING finger domain, PR: proline-rich domain.

FIG. 5 shows that PGC-1β bound to the central region of synoviolin having a unique and preserved domain in synoviolin (236 to 270 amino acid sequences, hereinafter referred to as "SyU domain"). Further, FIG. 5 shows that only the SyU domain is necessary for binding to the PGC-1β and that the modified synoviolin which lack the SyU domain in syno ΔTM (Syno ΔTMΔSyU) cannot bind to PGC-1β. Accordingly, it was indicated that the SyU domain is a minimum domain for binding to PGC-1β.

Example 6: Binding Between Synoviolin and PGC-1β In Vivo

Whether synoviolin and PGC-1β actually form a complex in in vivo was investigated. Specifically, a plasmid for expressing PGC-1β with HA tag (HA PGC-1β) and a plasmid for expressing synoviolin with FLAG tag (SYVN1/FLAG) or the modified synoviolin with FLAG tag (SYVN1ΔSyU/FLAG) were transfected in HEK-293T cells. Whole cell extract from the HEK-293T cells transfected with the expression plasmids was prepared to immunoprecipitate using anti-FLAG antibody. Proteins bound to the anti-FLAG antibody were eluted and separated by SDS-PAGE, and Western blot was performed using anti-HA antibody and the anti-FLAG antibody. The results were shown in FIG. 6A.

Figure 6A:
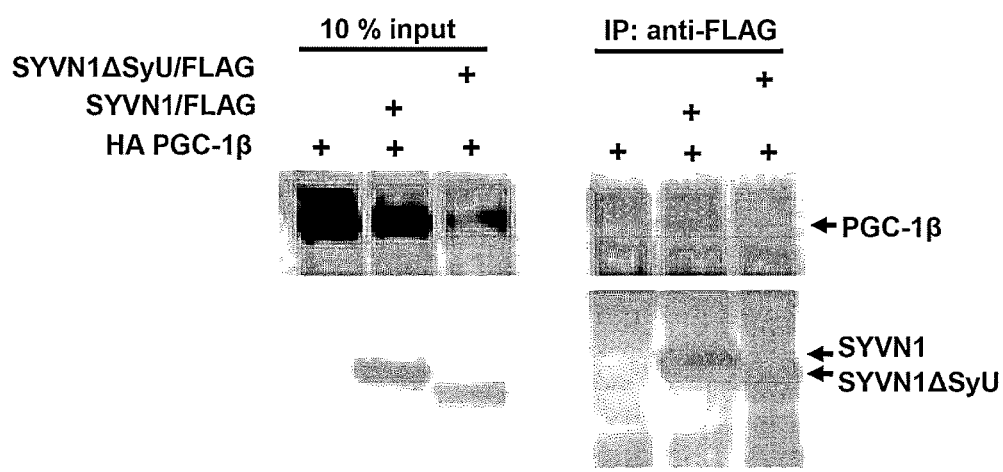
FIG. 6A is a result of Western blot showing binding between PGC-1β and synoviolin in vivo.

FIG. 6A shows that HA PGC-1β co-immunoprecipitated with the SYVN1/FLAG, but not with the SYVN1ΔSyU/FLAG. This indicates that the synoviolin (SYVN1) bound to the PGC-1β via the SyU domain in vivo.

In order to further investigate physical binding between synoviolin and PGC-1β, whole cell extract from the HEK-293 expressing synoviolin and PGC-1β was immunoprecipitated using anti-synoviolin antibody, and immuno blotting was performed using anti-PGC-1β antibody. The results were shown in FIG. 6B.

Figure 6B:
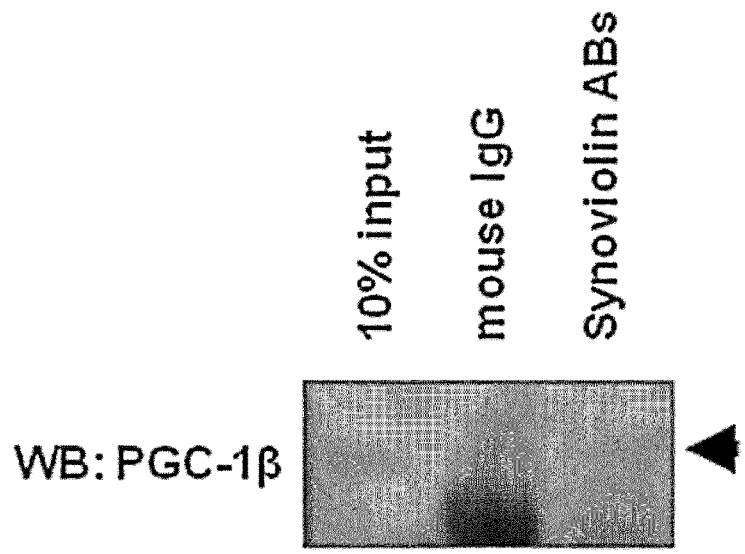
FIG. 6B is another result of Western blot showing binding of PGC-1β and synoviolin in vivo.

FIG. 6B shows that the endogenous PGC-1β was precipitated with the anti-synoviolin antibody and was detected. On the other hand, the endogenous PGC-1β was not detected in a case using non-immune mice IgG. This indicates that synoviolin can physically bind to the PGC-1β in in vivo.

Example 7: Subcellular Localization of Synoviolin and PGC-1β

It is known that synoviolin is ER resident protein and PGC-1β translocates into nucleus. Thus, subcellular localization of synoviolin and PGC-1β was investigated. Plasmids for expressing HA PGC-1β and/or syno/FLAG, synoviolin 3S/FLAG or synoviolin ΔSyU/FLAG were transfected in HEK-293T cells. After 24 hours, the subcellular localization of synoviolin and PGC-1β was investigated by immunofluorescence staining using anti-HA antibody and anti-FLAG antibody. The results were shown in FIG. 7.

Figure 7:
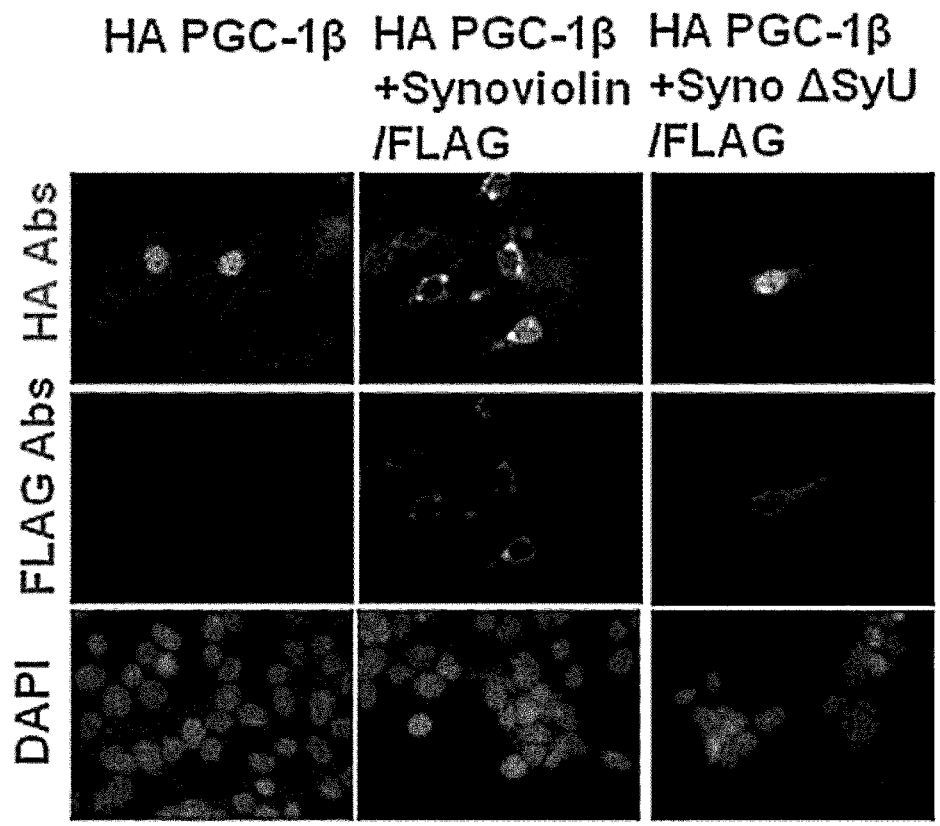
FIG. 7 is a fluorescence micrograph showing localization of PGC-1β and synoviolin.

FIG. 7 shows that HA PGC-1β was mainly localized in the nucleus in a case that HA PGC-1β alone was overexpressed in these cells, as reported previously (Kelly et al., 2009). On the other hand, in a case that HA PGC-1β was co-expressed with syno/FLAG, HA PGC-1β was predominantly co-localized with syno/FLAG in the perinuclear regions rather than the nucleus. In contrast, in a case that HA PGC-1β was co-expressed with Synoviolin ΔSyU/FLAG, HA PGC-1β was localized in the nucleus. Therefore, these results indicate that synoviolin entraps PGC-1β in the perinuclear regions, and that SyU domain is required for the sequestration in vivo.

Example 8: Ubiquitination of PGC-1β by Synoviolin

It is known that synoviolin is an E3 ubiquitin ligase (see Amano, T., et al. (2003). Synoviolin/Hrd1, an E3 ubiquitin ligase, as a novel pathogenic factor for arthropathy. Genes Dev. 17, 2436-2449). Then, whether PGC-1β is a substrate of synoviolin as the E3 ubiquitin ligase was investigated. In vitro ubiquitination assay was performed using in vitro transcribed/translated PGC-1β (FLAG-PGC), ubiquitin activating enzyme E1 (E1-His), ubiquitin binding enzyme E2 (UBE2G2-His), and ubiquitin (PK-His-HA-Ub), and the modified synoviolin fused to GST (syno(236-338)). The results were shown in FIG. 8A.

Figure 8A:
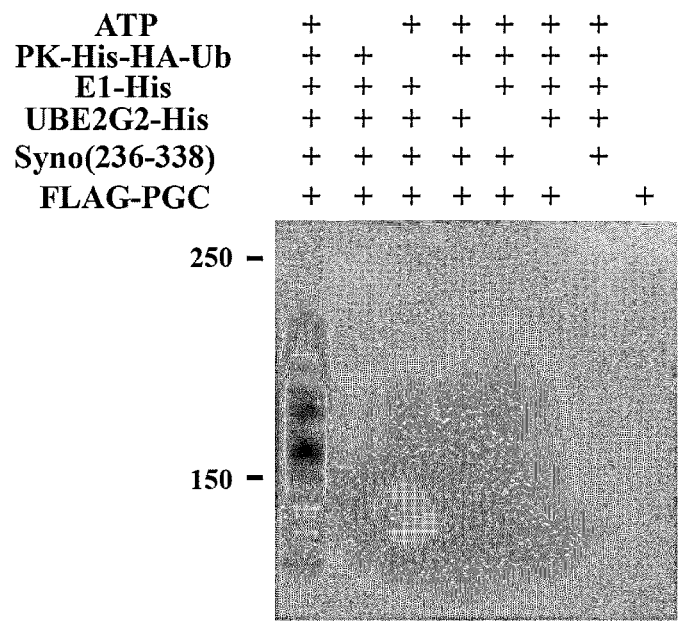
FIG. 8A is a result of Western blot showing ubiquitination of PGC-1β by synoviolin in vitro.

As shown in FIG. 8A, polyubiquitinated PGC-1β was detected under the condition with the presence of all of ATP, PK-His-HA-Ub, E1-His, UBE2G2-His, and syno(236-338). Accordingly, this indicates that PGC-1β is a substrate of synoviolin in vitro.

Next, ubiquitination of PGC-1β in vivo was investigated. Plasmids for expressing ubiquitin/FLAG, HA PGC-1, and synoviolin or synoviolin 3S were transfected in HEK-293T cells. Whole cell extract from the HEK-293T cell was immunoprecipitated using anti-HA antibody. Proteins bound to the anti-HA antibody were eluted and separated by SDS-PAGE, and Western blot was performed using anti-FLAG antibody. The results were shown in FIG. 8B.

Figure 8B:
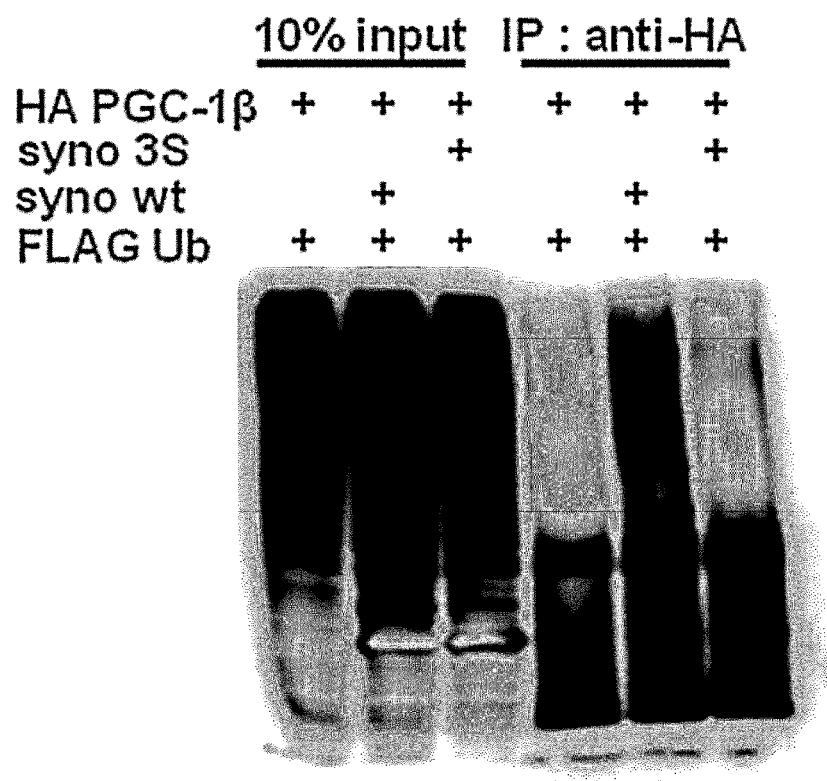
FIG. 8B is a result of Western blot showing ubiquitination of PGC-1β by synoviolin in vivo.

As shown in FIG. 8B, ubiquitinated HA PGC-1β was observed in cells expressing synoviolin WT, but not in cells expressing synoviolin 3S.

These results indicate that PGC-1β is a putative substrate of synoviolin in vitro and in vivo.

It is well known that ubiquitinated proteins are degradated in proteasome. Therefore, in order to investigate that the protein levels of PGC-1β was regulated by synoviolin, the following experiments were performed.

Western blot was performed to measure the protein levels of synoviolin and PGC-1β in epididymis and mesentery of mice in which synoviolin had knocked out after neonatal period (syno cKO).

Figure 8C:
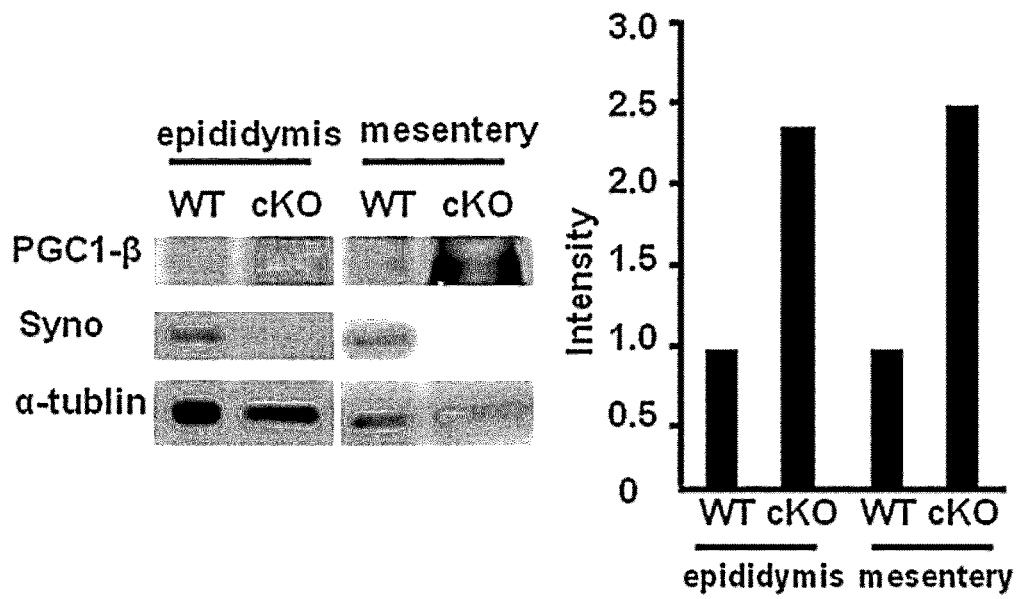
FIG. 8C is a result of Western blot showing an effect on protein levels of PGC-1β by synoviolin knockout in vivo.

FIG. 8C indicates that the protein level of PGC-1β in white adipose tissue from the synoviolin knockout mice was dramatically elevated than that from wild type mice. Transcriptional level of PGC-1β was not significantly different between the synoviolin knockout mice and the wild type mice.

Next, mRNA and protein levels of PGC-1β in mouse post-neonatal skin fibroblasts were investigated.

Skin fibroblasts from syno CKO mice were cultivated in DMEM medium and treated by tamoxifen (Tam) or solvent (DMSO) for 48 hours. Cell extracts or total RNA were collected, each was used for western blot and real-time PCR, respectively. The results were shown in FIG. 8D.

The protein level of PGC-1β was markedly increased in Tam-treated skin fibroblasts from synoviolin conditional knockout mice (1.4 folds). As expected, no change was observed in mRNA level of PGC-1β.

Further, in order to investigate whether PGC-1β was involved in synoviolin-mediated degradation of PGC-1β in cells, after the treatment by tamoxifen or solvent in the above experiment, 10 μM of MG-132, which is a proteasome inhibitor, was added and treated for two hours, and then, similar experiment was performed.

Figure 8D:
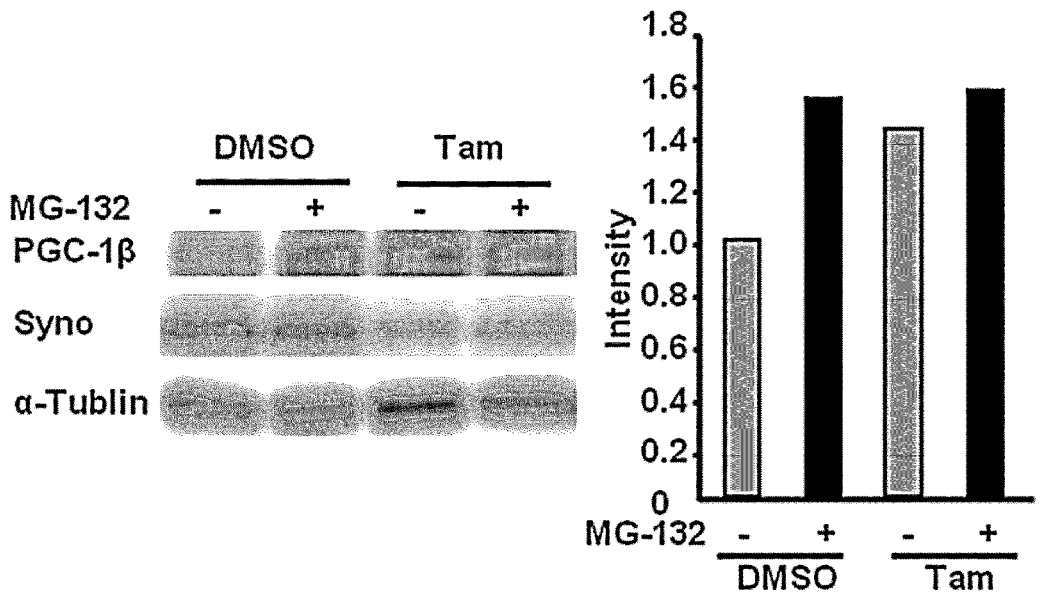
FIG. 8D is a result of Western blot showing an effect on PGC-1β protein degradation by synoviolin knockout in vivo.

FIG. 8D indicates that MG-132 indeed upregulated the protein level of PGC-1β in the solvent-treated (DMSO-treated) skin fibroblasts as well as in the tamoxifen-treated cells (1.6 folds). No additive effect was observed between the tamoxifen treatment and the addition of MG-132 (1.1 folds).

These results indicate that the protein level of PGC-1β is negatively regulated by synoviolin at posttranscriptional process and strongly suggest that the synoviolin is a major E3 for PGC-1β in cells.

Example 9: Effect of Synoviolin siRNA on PGC-1β Functions

In addition to the effect of lacking a portion of the gene, effect of siRNA (Syno siRNA) for synoviolin was confirmed by the following experiment.

Firstly, synoviolin knock down was performed by siRNA in HEK 293 cells. Synoviolin siRNA was prepared in accordance with already reported article (see, Yamasaki, S., et al. (2007). Cytoplasmic destruction of p53 by the endoplasmic reticulum-resident ubiquitin ligase 'Synoviolin'. EMBO J 26, 113-122.). Transfection of siRNA into cells was performed in accordance with a protocol with Lipofectamine 2000 (Invitrogen, Corporation). The results were shown in FIG. 9A.

Figure 9A:
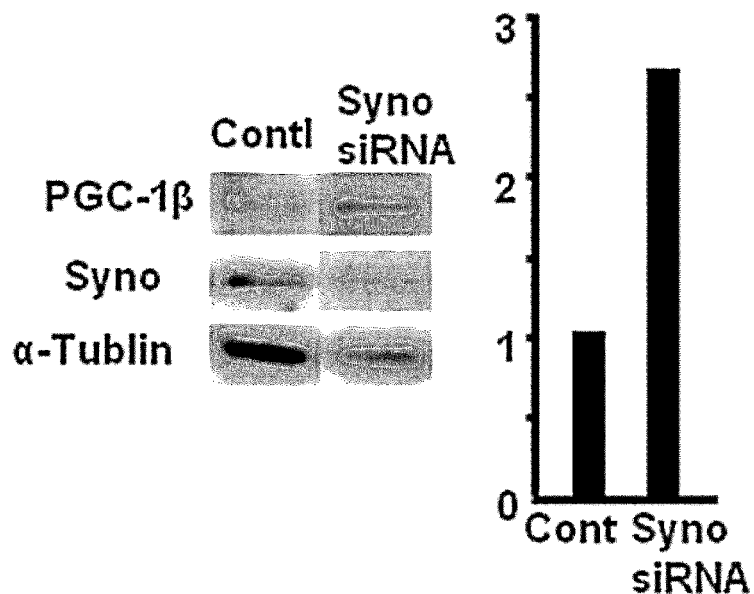
FIG. 9A is a result of Western blot showing an effect on PGC-1β protein expression by synoviolin siRNA.

FIG. 9A shows that synoviolin expression in Syno siRNA-treated cells was disappeared almost completely. In addition, PGC-1β protein level was increased 2.5 folds in Syno siRNA-treated cells. On the other hand, the expression of PGC-1β mRNA was not changed by treatment with syno siRNA.

It was known that PGC-1β has a function as a transcription coactivator of some transcription factors such as PPARα and PPARγ, and that PGC-1β was involved in various biological phenomena including mitochondrial biogenesis, β-oxidation, and weight control (see Scarpulla, R. C. (2008). Transcriptional paradigms in mammalian mitochondrial biogenesis and function. Physiol. Rev. 88, 611-638.). Therefore, PGC-1β was hypothesized to be a factor that causes the observed phenomena in syno cKO mice. In order to verify this hypothesis, two representative PGC-1β mediated cellular phenomena which were disturbed in syno cKO were analyzed. One is coactivator activity of PGC-1β and another is mitochondrial biogenesis.

Figure 9B:
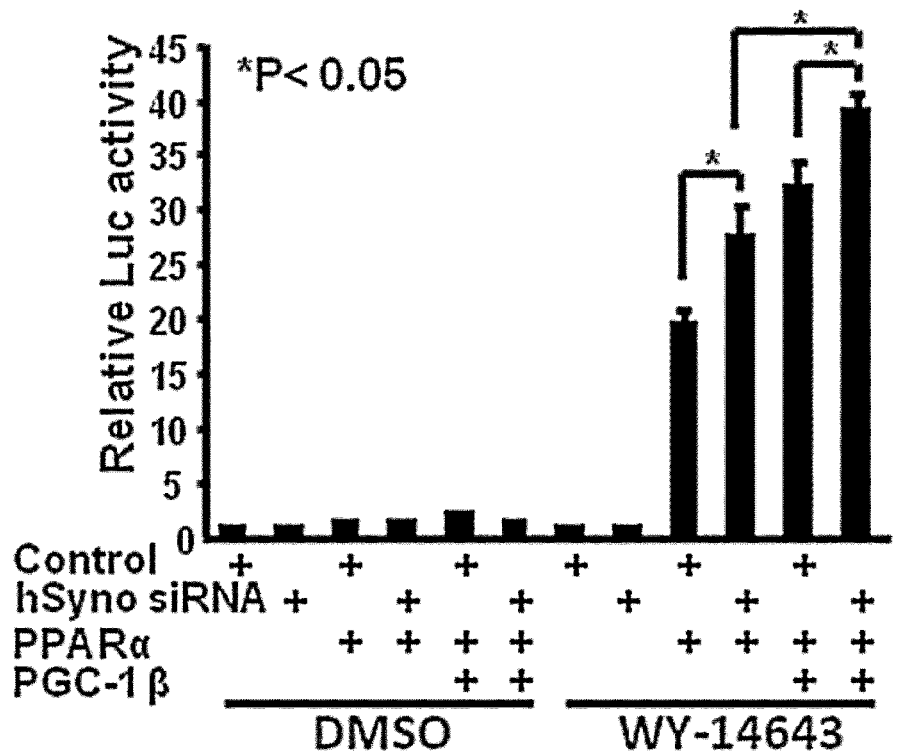
FIG. 9B is a result of Western blot showing an effect on functional expression of PGC-1β by synoviolin siRNA.

Specifically, control siRNA or Syno siRNA was temporarily transfected in HEK-293 cells. Reporter plasmid containing PPAR binding sites (PPRE x3-TK-luc), CMV-β-gal expression construct, or siRNA was temporarily transfected in HEK-293 cells. After 16 hours, DMSO or Wy-14643 was treated for 6 hours, and then Luciferase assay was performed (FIG. 9B).

It is known that PPAR-luciferase (PPRE x3-TK-luc) contains 3xPPAR binding sites, and that it was strictly regulated by PPAR, their ligands and the coactivators (see Kim, J. B., et al. (1998). ADD1/SREBP1 activates PPAR gamma through the production of endogenous ligand. Proc. Natl. Acad. Sci. USA 95, 4333-4337.).

Figure 9C:
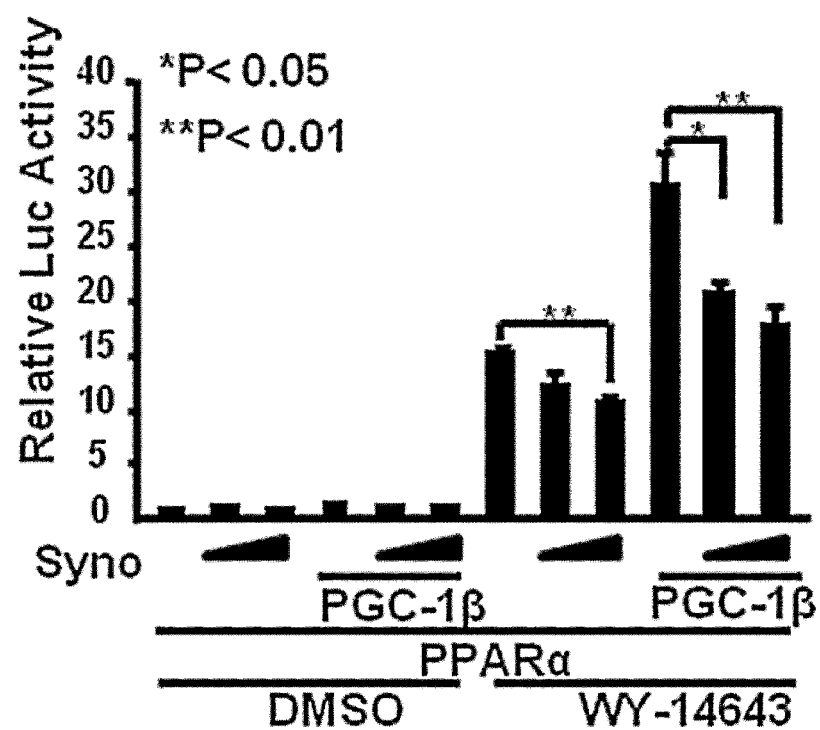
FIG. 9C is a graph showing an effect on functional expression of PGC-1β by overexpression of synoviolin.

In addition, in order to investigate the effect of synoviolin overexpression, the amount of vector for expressing synoviolin was increased in stages and co-transfected in the experiment (FIG. 9C).

After 16 hours from the transfection, cells were treated with solvent (DMSO) or Wy-14643 for 6 hours and the Luciferase assay was performed.

FIG. 9B shows that Wy-1463, which is one of PPARα agonists, induced PPRE x3-TK-luc reporter activity as reported previously (see Lin, J., et al. (2003). PGC-1beta in the regulation of hepatic glucose and energy metabolism. J Biol. Chem. 278, 30843-30848). Transfected Syno siRNA significantly enhanced the reporter activity, but control siRNA did not enhance the reporter activity, under the Wy-14643 induction. Co-transfected PGC-1β with Syno siRNA further enhanced the reporter activity.

FIG. 9C shows that synoviolin overexpression inhibited PGC-1β mediated coactivator functions.

These results indicate that synoviolin knockdown enhances PPARα mediated transcription through a pathway depending on PGC-1β.

Further, in order to verify whether the synoviolin knockdown regulates mitochondrial biogenesis in cells, synoviolin siRNA treated cells, which had been treated similar to the above, were observed with an electron microscope. The resulting pictures were shown in FIG. 9D.

Figure 2:
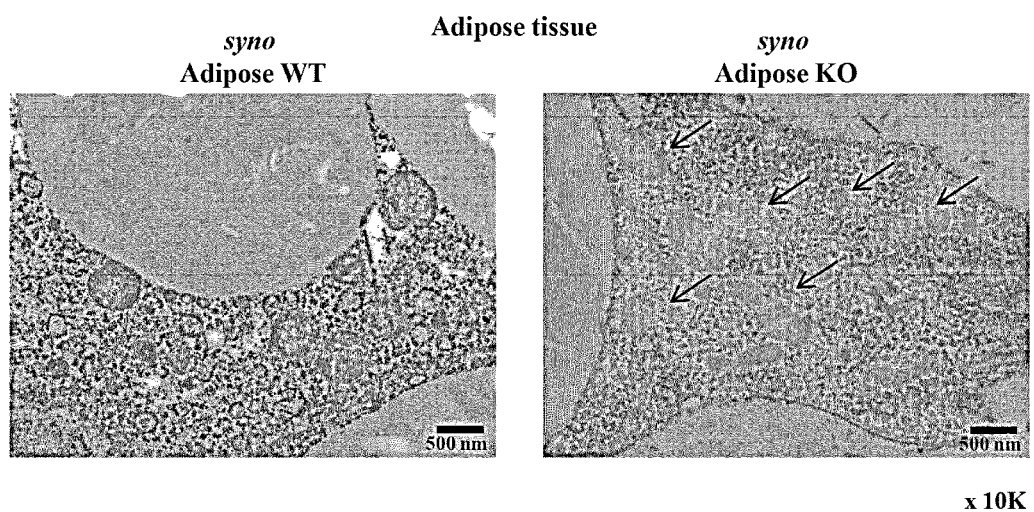
FIG. 2 is electron micrographs of mitochondria in white fat cells from the synoviolin knockout mice. The photograph on the left side shows the mitochondria in control wild-type mice (syno WT), and the photograph on the right side shows one in synoviolin knockout mouse (synocKO). The observation was performed at 5,000 fold magnification.
Figure 9D:
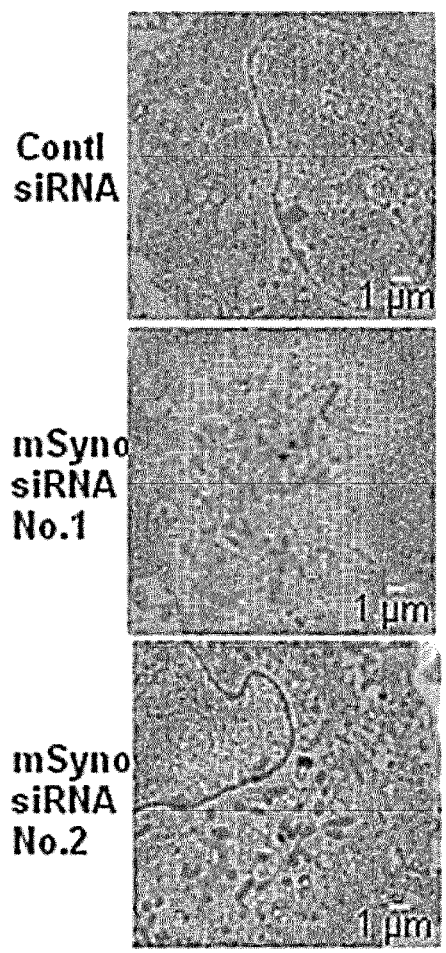
FIG. 9D is electron micrographs showing morphology changes of mitochondria by synoviolin siRNA.

FIG. 9D shows that the number and volume density of mitochondria was increased in the Syno siRNA treated cells as compared to the siRNA treated cells as a control, similar to the case in the white fat cell from syno cKO (FIG. 2).

Example 10: Inhibition of Binding Between Synoviolin and PGC-1β by Inhibitor of E3 Ubiquitin Ligase Activity of Synoviolin In order to investigate an influence on PGC-1β functions by inhibitor of E3 ubiquitin ligase activity of synoviolin, an effect on inhibition of binding between the synoviolin and the PGC-1β was firstly investigated. Specifically, in a usual binding assay using MBP-PGC-1β-His protein and GST-Syno ΔTM protein, LS-102 (PARMACOPIEA, Corporation) was added and these proteins were incubated for 12 hours. Then, these proteins were separated by SDS-PAGE of 12% gel concentration, and Western blot was performed. Anti-GST antibody diluted 2500 folds were used as a primary antibody, and anti-rat HRP diluted 10000 folds was used as a secondary antibody. The results were shown in FIG. 10.

The LS-102 is a compound represented by the following structural formula and is a chemical compound which selectively inhibits E3 ubiquitin ligase activity of synoviolin.

[Chemical Formula 4]

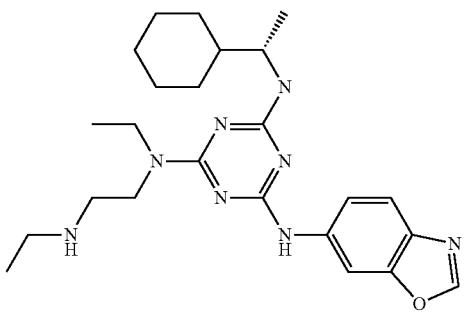

Figure 10:
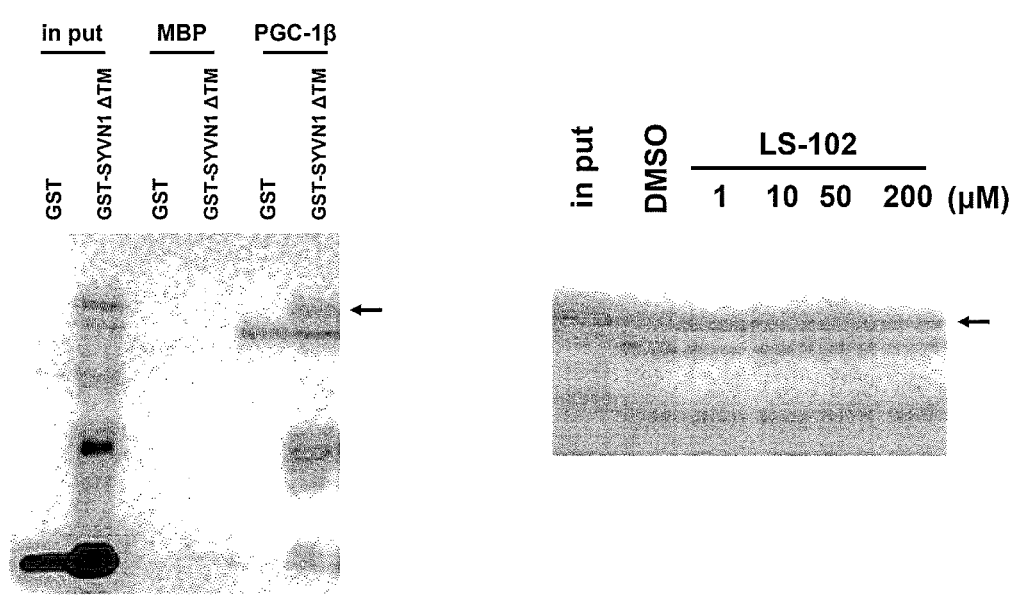
FIG. 10 is a result of Western blot showing a binding inhibition effect between synoviolin and PGC-1β by an E3 ubiquitin ligase activity inhibitor of synoviolin.

FIG. 10 shows that LS-102 has an effect on inhibition of binding between synoviolin and PGC-1β.

Example 11: Screening of Substances which Inhibit the Binding Between Synoviolin and PGC-1β

In order to obtain a substance which inhibits the binding between synoviolin and PGC-1β, with respect to the substances shown in the following table 2 included in screening library relating to E3 ubiquitin ligase, in order to examine influence on the binding between synoviolin and PGC-1β, in vitro binding assays similar to the examples 3 to 6 were performed. The results were shown in FIGS. 11-1, 11-2, 11-3, and 11-4. In this example, 2 μg of PGC-1β (see FIG. 4) and 2 μg of GST-Syno ΔTM (see FIG. 6) were used.

Figures 1, 11:
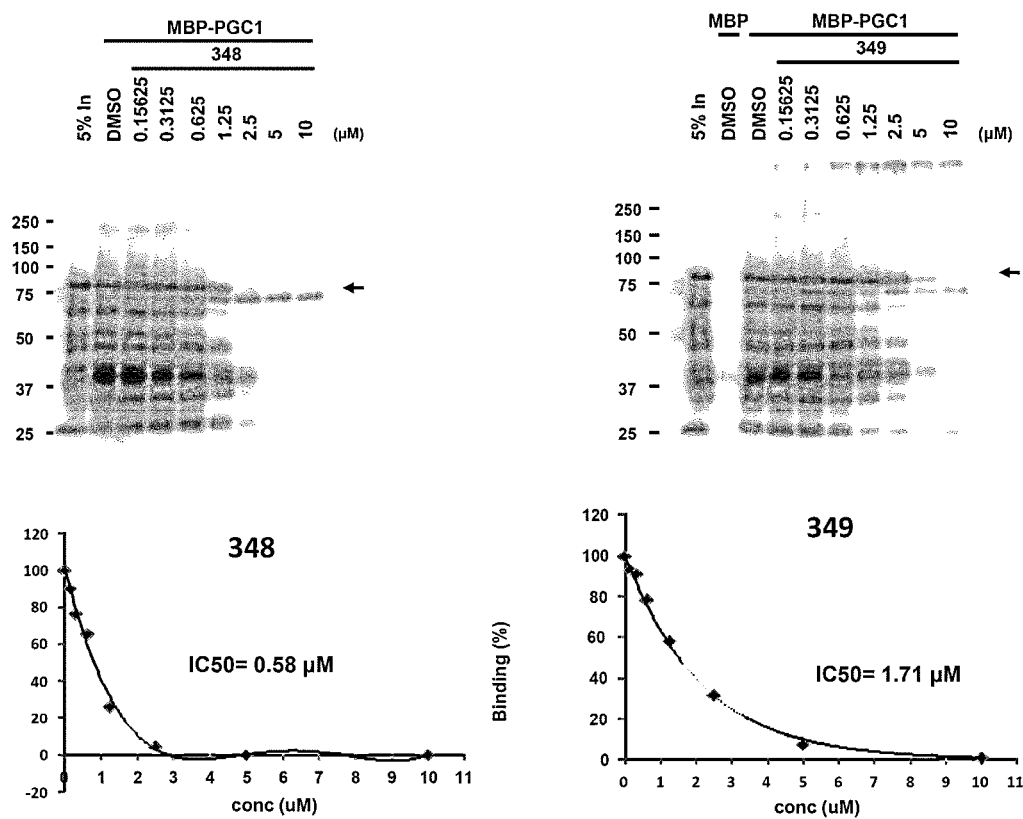
Figures 2, 11:
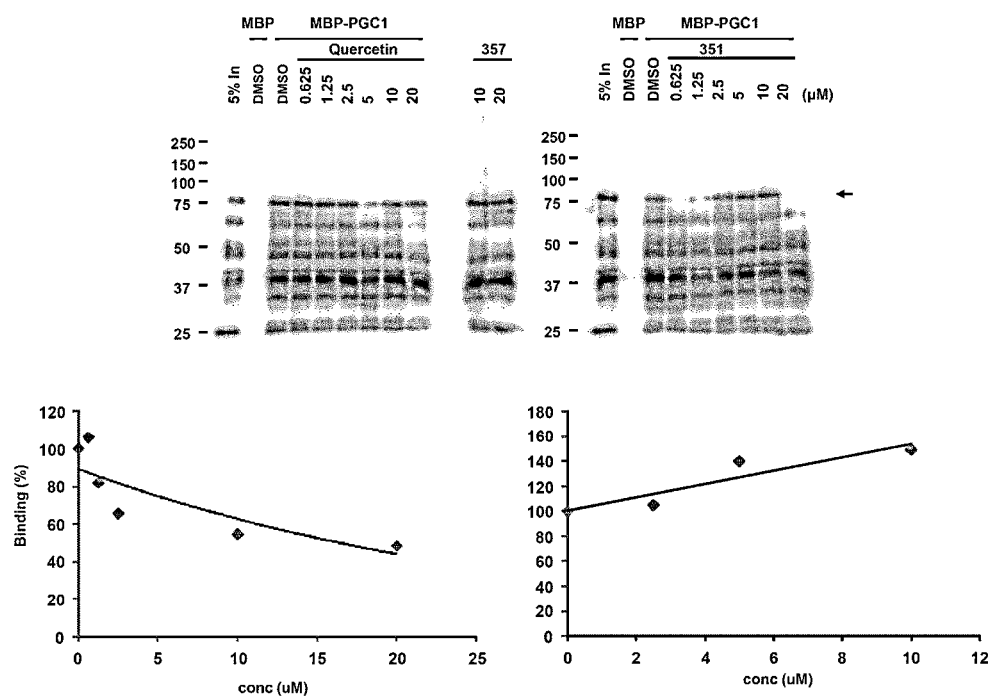
Figures 3, 11:
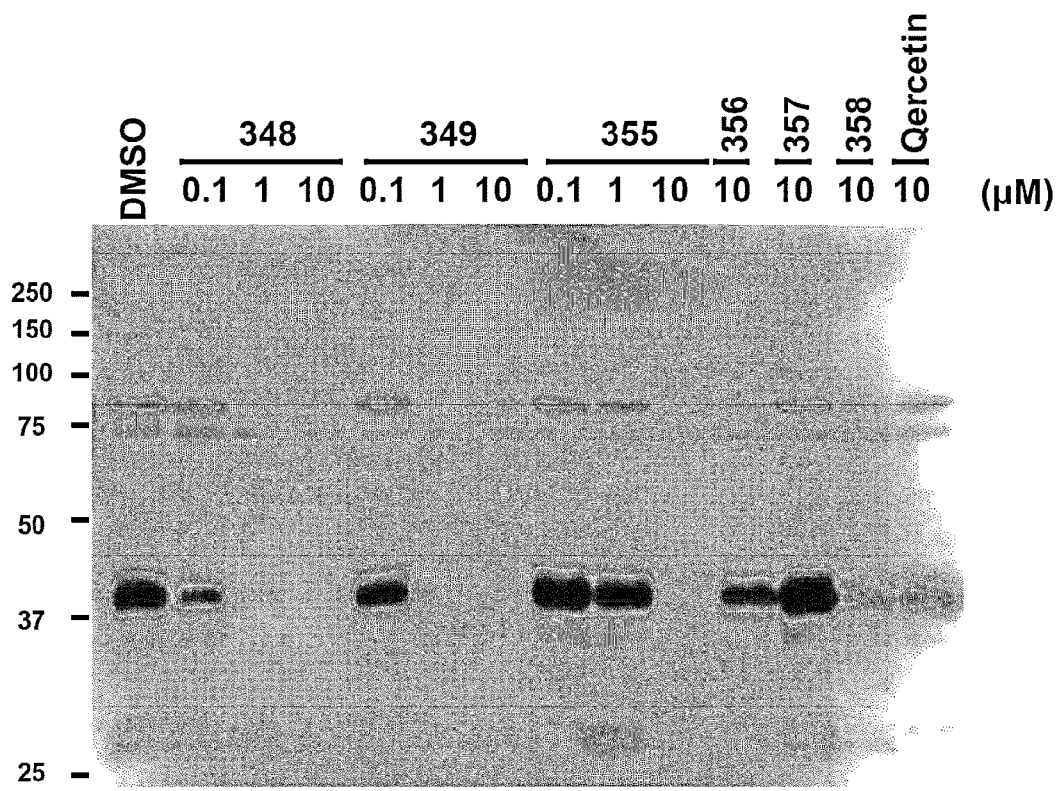
Figures 4, 11:
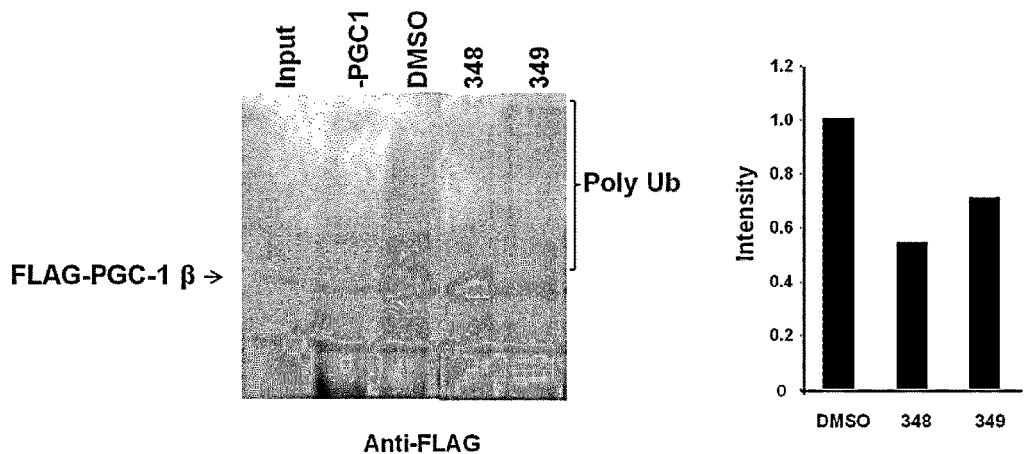

FIG. 11-1 shows Western blot indicating an effect on inhibition of the binding between synoviolin and PGC-1β by test substances 348 and 349 (upper diagram), and a graph evaluating binding capacities of the test substances 348 and 349 (lower diagram). FIG. 11-2 shows Western blot indicating an effect on inhibition of the binding between synoviolin and PGC-1β by test substances quercetin and 351 (upper diagram), and a graph evaluating binding capacities of the test substances quercetin and 351 (left and right of lower diagram). FIG. 11-3 shows Western blot indicating effects on inhibition of binding of each of the test substances.

TABLE 2

| Name of substance | Structure | Supplier |
|---|---|---|
| 348 (B) | (OH, O / OH, O naphthoquinone diol) | SIGMA |
| 349 (C) | (O / OH, O naphthoquinone ol) | SIGMA |

TABLE 2-continued
| Name of substance | Structure | Supplier |
|---|---|---|
| 351 (E) | 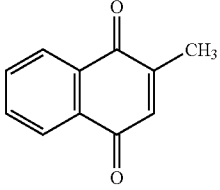 | SIGMA |
| 355 | 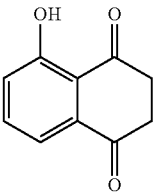 [SMILES: O=C1CCC(=O)c2c(O)cccc21] | ShanghaiChemPartnerCo. |
| 356 | 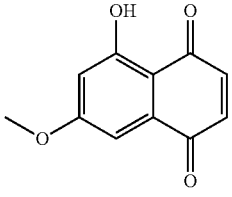 | ShanghaiChemPartnerCo. |
| 357 | 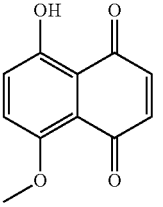 | ShanghaiChemPartnerCo. |
| 358 | 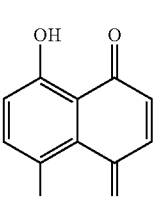 | ShanghaiChemPartnerCo. |
| Quercetin | 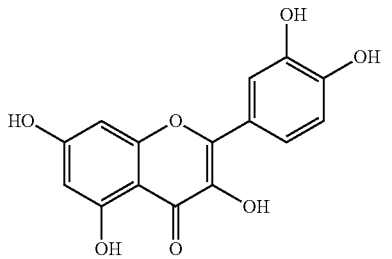 [SMILES: O=c1c(O)c(-c2ccc(O)c(O)c2)oc2cc(O)cc(O)c12] | |

FIGS. 11-1 to 11-4 show the effects of 348, 349, 355, 358, and quercetin on inhibition of the binding between synoviolin and PGC-1β. It was also understood that 351 enhances the binding. FIG. 11-4 shows that polyubiquitination of PGC-1β has been suppressed by using 348 and 349 as compared to control group (DMSO).

Example 12: Influences of Inhibitor of E3 Ubiquitin Ligase Activity of Synoviolin and Substances which Inhibit the Binding Between Synoviolin and PGC-1β on PGC-1β Functions The luciferase assay was performed similar to the example 9 except for using 5 μM of LS-102, 0.1 μM and 0.5 μM of 348, 0.1 μM and 5 μM of 349, and 5 μM of 351 and 355 instead of transfecting the Syno siRNA in the example 9. The same volume of DMSO, which is a solvent of each compound, was added as a control. The results were shown in FIG. 12.

Figure 12:
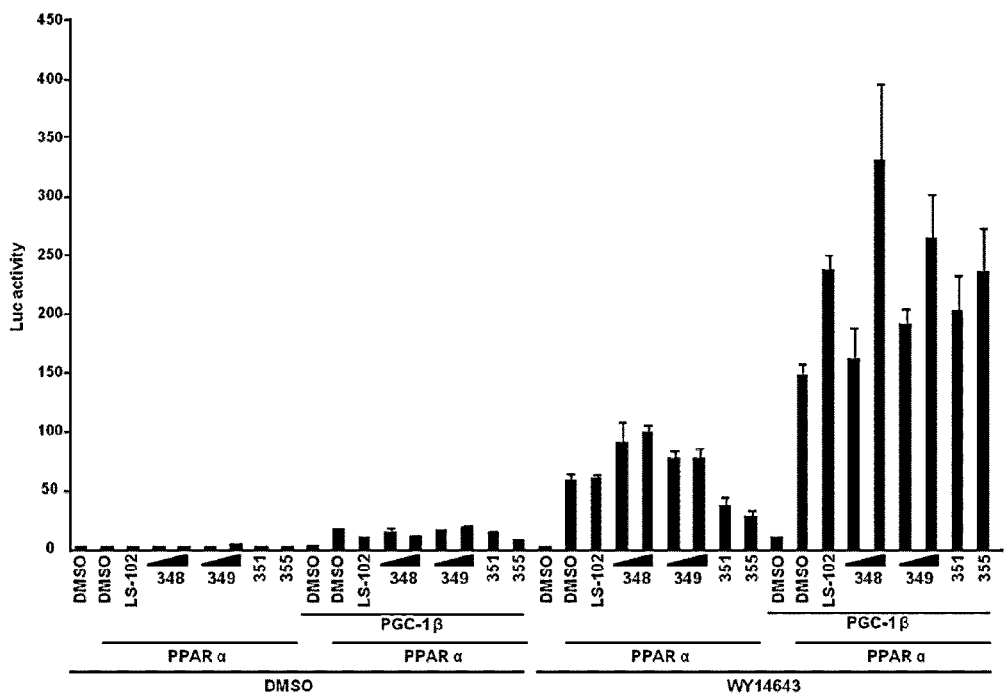
FIG. 12 is a graph showing effects on PGC-1β function by test substances.

FIG. 12 shows that luciferase activity was lowered only in a case of treating by 351 among the cases of treating by the compounds. These results indicate that a substance, which enhances the PGC-1β function by inhibiting the binding between the synoviolin and the PGC-1β, has been obtained.

When a protein level of the PGC-1β was investigated as a confirmation, the protein level of the PGC-1β was doubled in LS-102 treated cells. On the other hand, the expression of PGC-1β mRNA was not changed by the LS-102 treatment.

Figure 13:
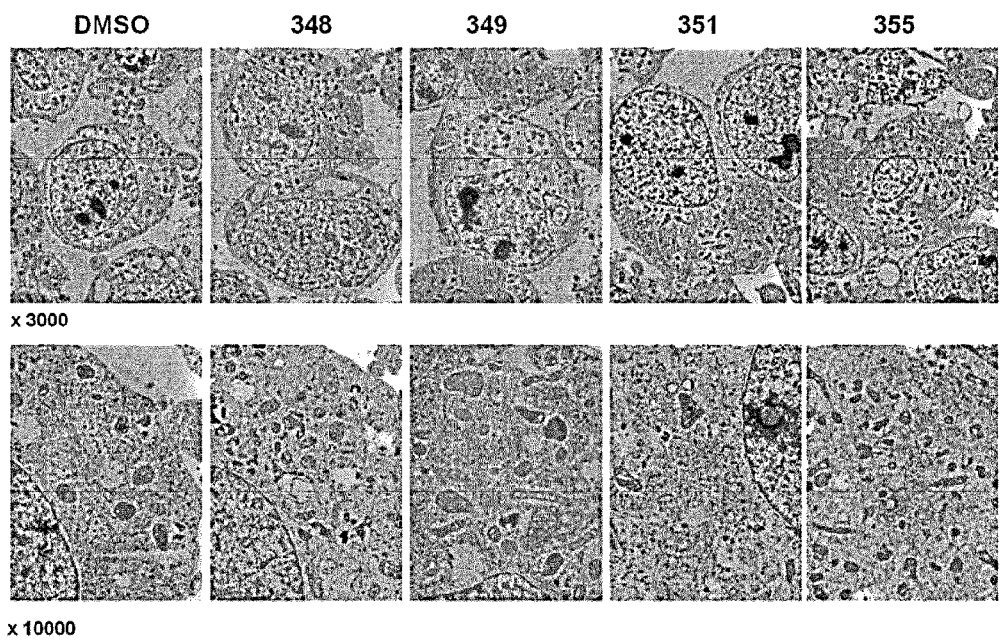
FIG. 13 shows electron micrographs showing morphology changes of mitochondria by test substances.

Example 13: Influences of Substances which Inhibit the Binding Between Synoviolin and PGC-1β on Mitochondrial Functions The observation of mitochondria was performed similar to the example 9 except for observing after 72 hours from adding 1 μM of 348, 349, 351 and 355 to cells instead of transfecting the Syno siRNA in the example 9. The resulting pictures were shown in FIG. 13. FIG. 13 shows that proliferation (increase in the number) of mitochondria or increase in size of mitochondria has been observed by addition of in 348, 349, and 355. These results suggest that the suppression of the synoviolin enhances the activity of transcription coactivator PGC-1β and activates mitochondria, namely, being a molecular target of novel drug discovery of agonist.

Example 14: Effect of the Inhibition of Synoviolin Expression and Inhibition of Ubiquitination Activity 3T3-L1 cells, which are preadipocytes of mice, were cultivated in Dulbecco's Modified Eagle Medium (DMEM; High Glucose) containing 10% fetal bovine serum (FBS) for 3 days after reaching confluent state. 500 μM of isobutyl-methylxanthine (IBMX), 1 μM of Dexamethasone, and 5 μg/mL of insulin were added to induce differentiation. At the same time, 10 μM of LS-102 (ubiquitination activity inhibitor of synoviolin) or DMSO was added. After cultivation for 3 days, the medium was replaced with medium containing 4 μg/mL of Insulin, and 10 μM of LS-102 or DMSO was added. After cultivation for 3 days, the medium was replaced with DMEM (High Glucose) containing 10% FBS to cultivate for 3 days. As siRNA treatment, 200 pmol of siRNA Syno770 (sense strand consists of the following SEQ ID NO: 2) was introduced using the Lipofectamine2000 two days before induction of differentiation.

SEQ ID No. 2:    5'-GCUGUGACAGAUGCCAUCA-3'

After the cultivated 3T3-L1 cells were washed with PBS(-) (Phosphate Buffered Saline solution from which magnesium and calcium had been eliminated), the cells were fixed by 10% formalin. The cells were washed with the PBS(-) to be replaced with 60% isopropanol. After staining for 20 minutes with 18 mg/ml of Oil Red O (isopropanol was used as solvent), the cells were washed with 60% isopropanol and PBS(-), and observed by a microscope.

In the cells in which the synoviolin gene activity was inhibited by siRNA, the number of differentiated adipose cells was less as compared to a control, and the differentiation was suppressed. Further, lipid droplets, which were not observed in normal adipocytes, in the form of annular ring were observed. These results indicate that synoviolin gene expression and self-ubiquitination of synoviolin protein were inhibited.

Example 15: Oxygen Consumption of Adipocyte in Synoviolin Knockout Mice

In order to investigate whether mitochondrial functions are activated in CAG-Cre-ER;Syvn1$^{flox/flox}$ mice, oxygen consumption per one cell of adipocytes was measured.

(Measuring Method of Oxygen Consumption)

Figure 14:
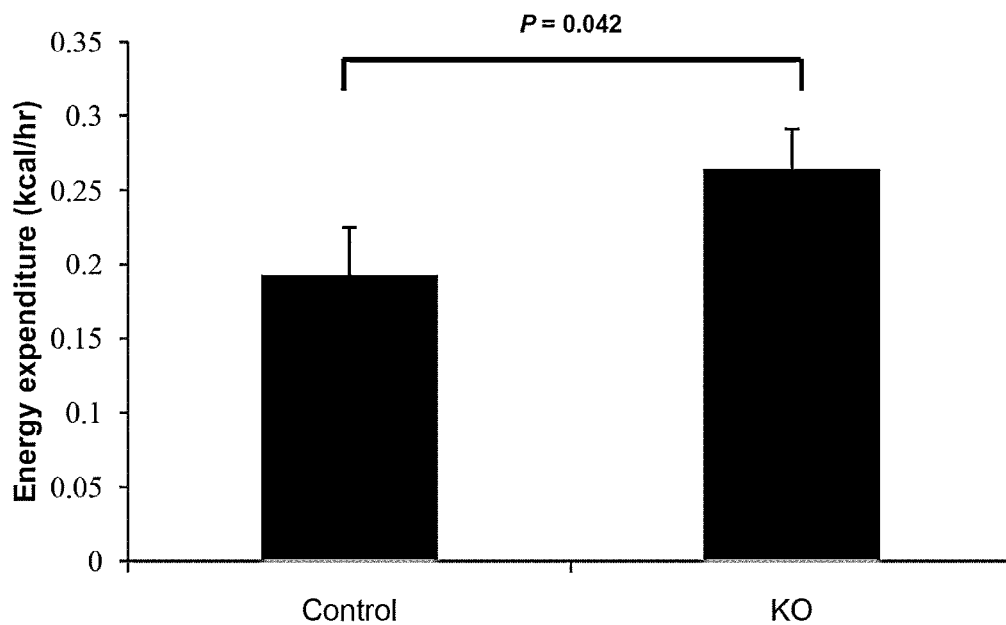
FIG. 14 is a graph showing an oxygen consumption of adipocytes in synoviolin knockout mice.

Measuring method of oxygen consumption was as follows. Subcutaneous fat was collected from CAG-Cre-ER; Syvn1$^{flox/flox}$ mice and control mice to obtain single cell by treating 0.1% (w/v) collagenase at 37° C. for 1 hour. For a suspension of the obtained single cells, oxygen consumption was measured by using MitoXpress (registered trademark)-Xtra-HS (Luxcel Biosciences Ltd. Ireland) according to a manual attached to a kit. The results were shown in FIG. 14. FIG. 14 is a graph showing oxygen consumption of the adipocyte in synoviolin knockout mice. Adipocytes of primary mouse were isolated to measure oxygen consumption in one cell of the adipocytes. Statistical process was performed by an unpaired t-test.

FIG. 14 shows that the oxygen consumption of the adipocytes from the CAG-Cre-ER;Syvn1$^{flox/flox}$ mice has been significantly larger as compared to that from the control mice.

Example 16: Base Metabolic Rate in Synoviolin Knockout Mice

Figure 15:
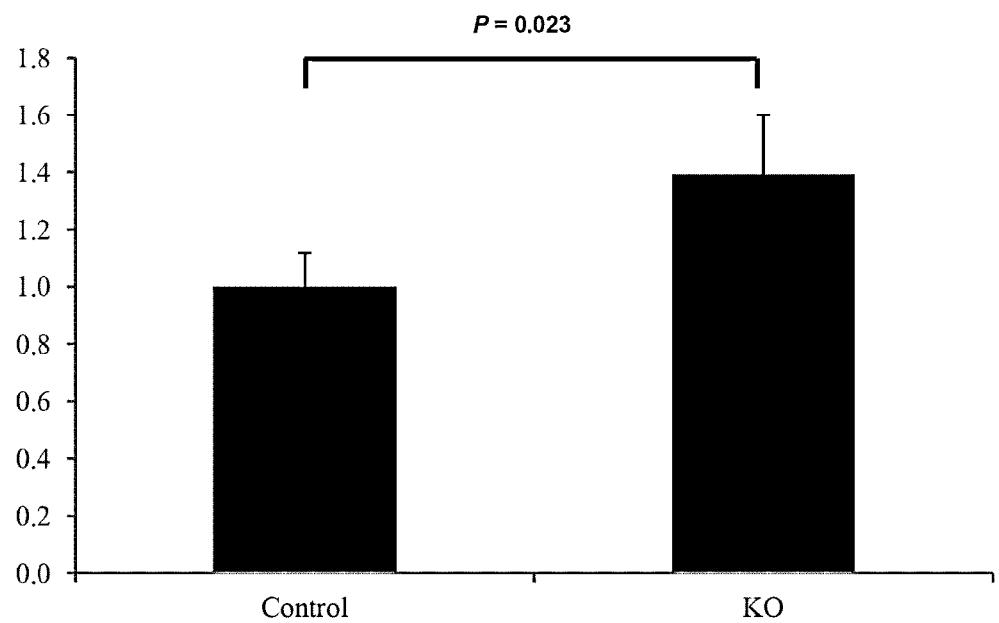
FIG. 15 is a graph showing a basal metabolic rate in synoviolin knockout mice.

In order to investigate whether mitochondrial functions are activated in CAG-Cre-ER;Syvn1$^{flox/flox}$ mice, the base metabolic rate of CAG-Cre-ER;Syvn1$^{flox/flox}$ mice was measured (FIG. 15).

(Measuring Method of Base Metabolic Rate)

Measuring method of the base metabolic rates was as follows. By using mice of 7 days after Tam administration, oxygen consumption ($VO_2$) and production amount of carbon dioxide ($VCO_2$) in a case of fasting for 4 hours and being rest were measured by Oxymax Equal Flow System (Columbus Instruments, 950 N. Hague Ave; Columbus, Ohio USA). Further, motor activity (the number of motion) was measured together using DAS system (Neuro Science, Inc., Japan). FIG. 15 is a graph showing the base metabolic rates in the synoviolin knockout mice. Statistical process was performed by an unpaired t-test.

As shown in FIG. 15, the base metabolic rates of the CAG-Cre-ER; Syvn1$^{flox/flox}$ mice have been significantly larger as compared to the base metabolic rates of the control mice. This result suggests that SYVN1 enhances the mitochondrial activity in vivo.

Example 17: Relation Between Synoviolin and Fat Burning

Figure 16:
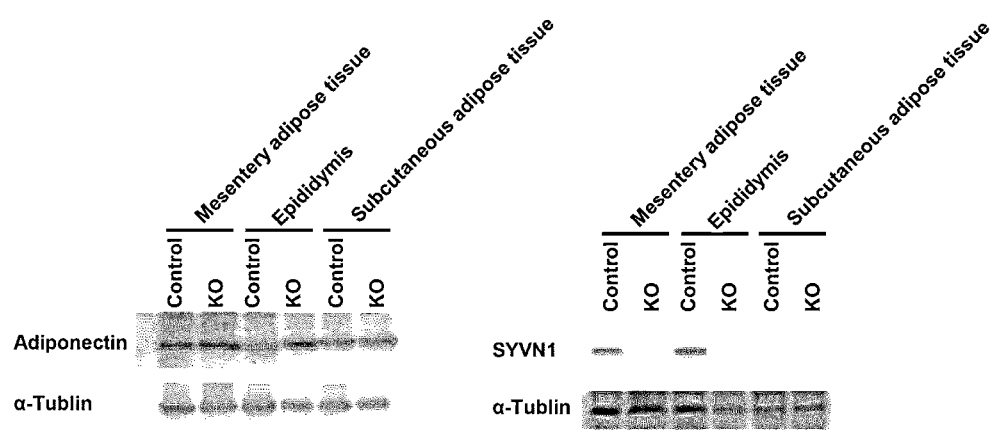
FIG. 16 shows photographs instead of diagrams illustrating the results of Western blot for detecting adiponectin and synoviolin in each tissue of wild-type WT and synoviolin KO.

In order to investigate adiponectin and synoviolin in each tissue of wild-type WT mice and synoviolin KO mice, Western blotting was performed. FIG. 16 is a photograph instead of a diagram illustrating the Western blotting of adiponectin and synoviolin in each tissue of the wild-type WT and the synoviolin KO. In the diagram, alpha-tubulin is used as an internal standard. From FIG. 16, it can be considered that knockout of the synoviolin causes the increase in the amount of the adiponectin and that combustion of fatty acid is promoted.

Example 18: Measurement of Half-Life of PGC-1β

In order to investigate whether the interaction between SYVN1 and PGC-1β is important for degradation of PGC-1β via SYVN1, the half-life of PGC-1β was measured.

Figure 17:
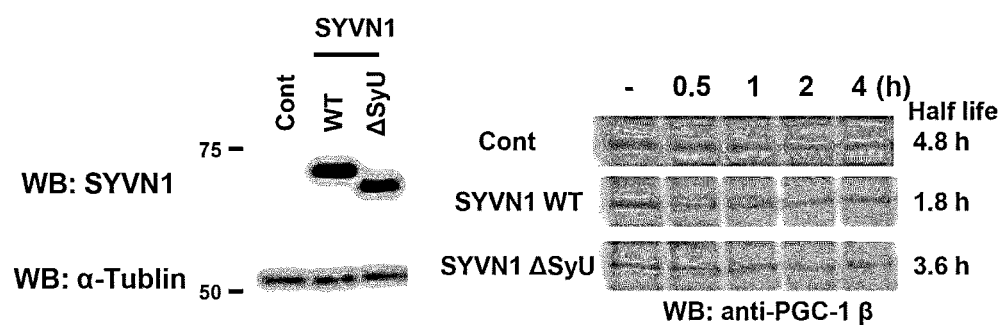
FIG. 17 shows a result of Western blot for measuring a half-life of PGC-1β.

A test was performed by modifying the conventional known method (Yamasaki, S., et al. EMBO J. 26, 113-122 (2007) and Bernasconi, R., et al. J. Cell Biol. 188, 223-235 (2010)) as follows. 1 μg of pcDNA3 Synoviolin/FLAG, empty vector, or 1.5 μg of pcDNA3 Synoviolin ΔSyU/FLAG and 0.75 μg of pcDNA3 HAPGC-1β were transfected in mouse embryonic fibroblasts (MEF Syno−/−) from synoviolin knockout mice. After 48 hours from the transfection, the cells were treated with 40 μM Cycloheximide for 0.5, 1, 2, or 4 hours and dissolved by buffer (10 mM Tris-HCl pH 8.0, 150 mM NaCl, 1 mM EDTA, 1% NP-40, 1 mM DTT, protease inhibitors) to be subjected to immunoblot analysis by anti-PGC-1β, anti-SYVN1, or anti-alpha-tubulin antibody. Each test was performed at least three times. The results were shown in FIG. 17. FIG. 17 shows that the wild-type synoviolin (SYVN1 WT) has extremely shortened the half-life of PGC-1β. FIG. 17 also shows that SYVN1 ΔSyU has not so promoted degradation of PGC-1β. Accordingly, the PGC-1β protein level has been shown to be negatively regulated through the binding to synoviolin in the process of post-transcription. Further, synoviolin has been strongly suggested to be a major E3 ligase of PGC-1β.

Figure 18:
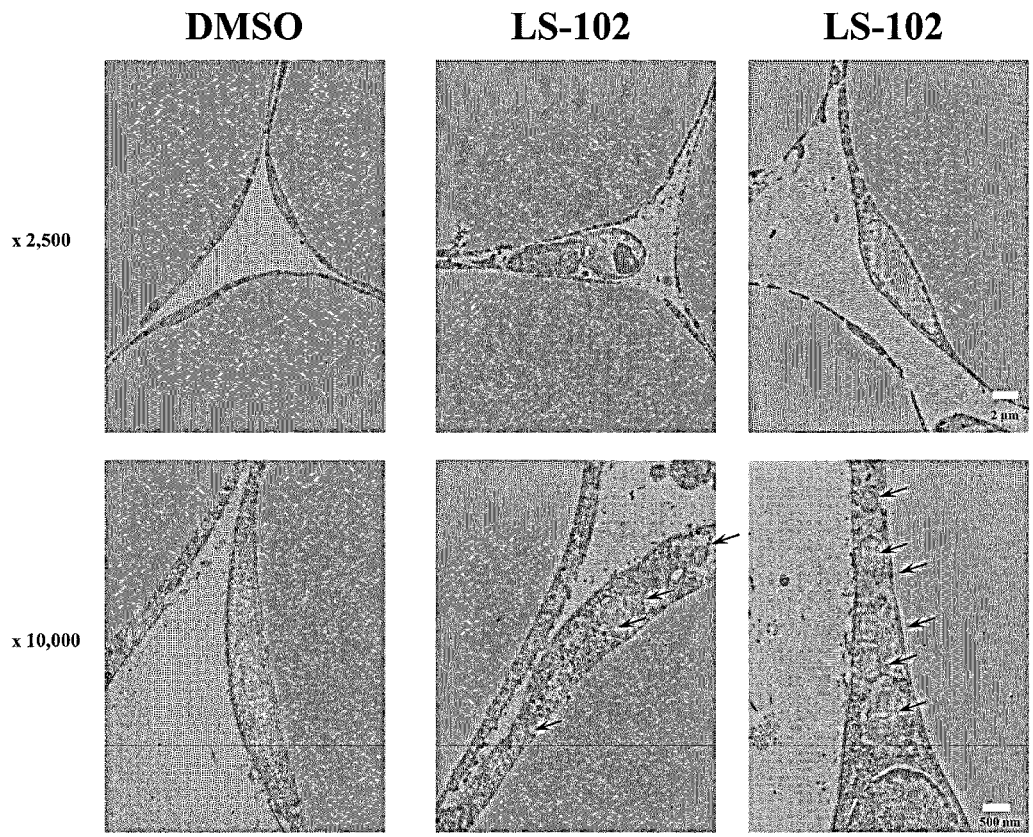
FIG. 18 shows electron micrographs showing the morphological changes of mitochondria in adipose tissues by LS-102.

Example 19: Influence of Ubiquitination Activity Inhibitor LS-102 of Synoviolin on Mitochondrial Functions 50 mg/kg body weight of LS-102 per day or solvent (DMSO) as a control was administered intraperitoneally to 7 to 8-week-old C57BL/6J mice to observe adipose tissue slices of the mice of fifty seventh day after the administration using a microscope. The results were shown in FIG. 18. FIG. 18 shows electron micrographs showing morphological changes of mitochondria in the adipose tissues by LS-102. Magnifications of the electron microscope were 2,500 folds and 10,000 folds and the white bars indicate scale bars (2 μm in the 2,500 folds and 500 nm in the 10,000 folds).

FIG. 18 shows that the LS-102 treatment has caused increases in number and volume density of mitochondria in the adipose tissue cells. This suggests that inhibition of E3 ligase activity of synoviolin by LS-102 has caused hyperactivation of PGC-1β to promote mitochondrial biogenesis.

Example 20: Half-Life of PGC-1β

Figure 19:
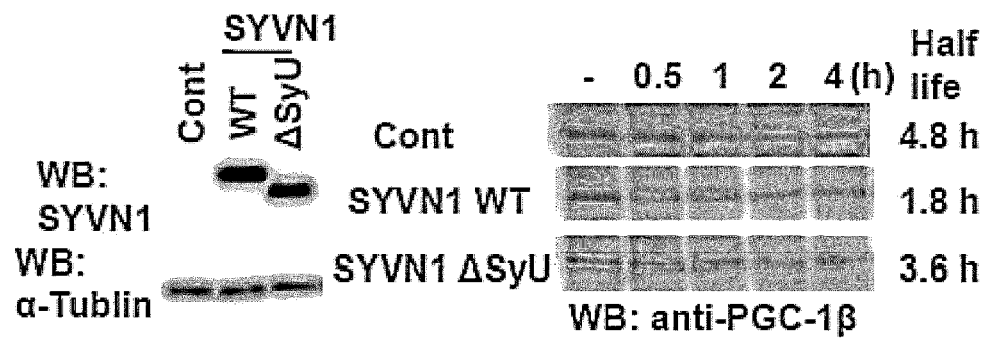
FIG. 19 is a result of Western blot showing a half-life of PGC-1β.

Empty vector (control: CONT), synoviolin wild-type (SYVN1 WT), and synoviolin unique domain (modified synoviolin in which the binding region with PGC-1β has been deleted: SYVN1 ΔSyU) were respectively transfected with expression vector of PGC-1β in mouse embryoinic fibriblasts (MEF) established from synoviolin KO mice in accordance with a conventional method. After 48 hours from the transfection, treatment with Cycloheximide (40 μM), which is a typical protein translation inhibitor, was performed for 0.5, 1, 2, and 4 hours as shown in FIG. 19, and then Western blot was performed for each cell extract. The results were shown in FIG. 19. FIG. 19 shows a western blotting showing the half-life of the PGC-1β. As shown in FIG. 19, the half-lives of the PGC-1β in cells were demonstrated to be 4.8 hours, 1.6 hours, and 3.6 hours, respectively.

This result shows that the half-life of the PGC-1β, namely degradation thereof has been regulated by existence of synoviolin, and that SyU domain is essential for the regulation.

Example 21: Evaluation of Ubiquitination

The binding assay was performed using the following assay system. 2 μg of MBP-PGC-1β His (1-367aa) and 2 μg of the modified synoviolin fused to GST were bound for 12 hours in a buffer (20 mM Tris-HCl pH 8.0, 100 mM NaCl, 1 mM EDTA. 0.1% NP-40, 5% glucose 1, and protease inhibitors) to detect PGC-1β using anti-PGC-1β antibody.

The ubiquitin assay was performed using the following assay system. E1-His 125 ng, UbcH5C 150 ng, MBP-SYVN1 ΔTM-His 150 ng, GST-PGC-1β (1-367 aa; GST-P5), and HA-ubiquitin (HA-Ub) 750 ng were reacted at 30° C. for 2 hours in a buffer (50 mM Tris-HCL pH 7.5, 5 mM MgCl$_2$, 0.6 mM DTT, and 2 mM ATP) to be ubiquitinated. Thereafter, the ubiquitinated proteins were bound to Gluta-thione Sepharose in GST washing buffer (50 mM Tris-HCl pH 7.5, 0.5 M NaCl, 1% Triton X, 1 mM EDTA, 1 mM DTT, and protease inhibitors). After washing with the GST washing buffer, ubiquitination of PGC-1β was detected by Western blotting using anti-PGC-1β antibody and anti-HA antibody. The results of in vitro ubiquitination assay were shown in FIG. 20.

FIG. 20 shows that synoviolin (SYVN1) has directly ubiquitinated PGC-1β.

Example 22: Inhibition of Ubiquitination of Test Substances

In order to examine the concentration dependency of the inhibiting activity of test substances 348 and 349 in PGC-1β ubiquitination by synoviolin (SYVN1), the in vitro binding assay was performed in the same manner as described in Example 11. FIG. 21 shows a result of western blot showing the concentration dependency of the inhibiting activity of the test substances 348 and 349 in PGC-1β ubiquitination. FIG. 21 shows that the inhibiting activity of the PGC-1β ubiquitination in 10 μM is higher than that in 1 μM in all of the test substance. Namely, the ubiquitination inhibiting activity of the test substances was shown to be concentration dependent.

Example 23: Binding Between the Fragmented and Modified Synoviolin and PGC-1β

The Example 5 showed the high possibility that synoviolin (SYVN1) binds to PGC-1β in the region of 236 to 270 (SyU domain). In this example, in order to find a portion to which the PGC-1β binds with high possibility from the SyU domain, the following example was performed.

Figure 23:
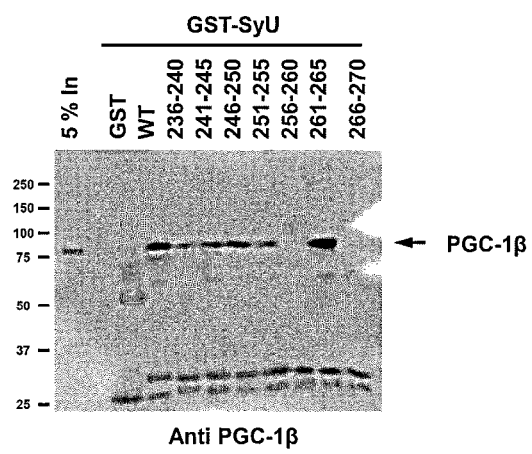
FIG. 23 is a result of Western blot using modified SYVN1 SyU.

FIG. 22 shows amino acid sequences of SyU domain of multiple species. The modified SYVN1 SyU, in which each five amino acids corresponding to portions of 236-240, 241-245, 246-250, 251-255, 255-260, 261-265, and 266-270 of synoviolin (SYVN1) had been replaced with alanine, and the PGC-1β were bound. The results were shown in FIG. 23. FIG. 23 shows a result of Western blot in the modified SYVN1 SyU. FIG. 23 shows that the portions of 256-260 and 266-270aa are important for binding with PGC-1⊕.

Example 24: Binding Between the Fragmented and Modified Synoviolin and PGC-1β

Figure 24:
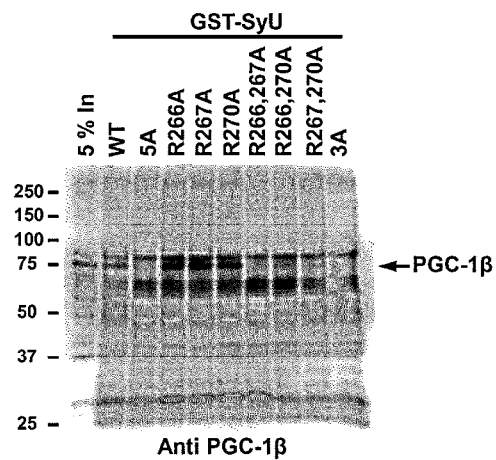
FIG. 24 is a result of Western blot using s modified SYVN1266-270aa.

Amino acid sequence of the portion of 266-270aa is RRAIR. Peptide consisting of the amino acid sequence of AAAAA (control), amino acid in $266^{th}$ R had been replaced with A (R266A), amino acid in $267^{th}$ R had been replaced with A (R267A), amino acid in $270^{th}$ R had been replaced with A (R270A), amino acid in $266^{th}$ R and $267^{th}$ R had been replaced with A (R266, 267A), amino acids in $266^{th}$ R and $270^{th}$ R had been replaced with A (R266, 270A), amino acids in $267^{th}$ R and $270^{th}$ R had been replaced with A (R267, 270A), and amino acids in the three R had been replaced with A (3A) was prepared, and Western blot was performed in the same manner as in the Example 5. The results were shown in FIG. 24. FIG. 24 is a result of Western blot in the modified SYVN1 266-270aa. FIG. 24 shows that at least two arginine residues are desirable for binding to the PGC-1β via the SYVN1 266-270aa.

INDUSTRIAL APPLICABILITY

The mitochondrial function regulator of the present invention causes increases in number and size of mitochondria, enhances β-oxidation of the fatty acid and the mitochondrial biogenesis, and can be applied to treatment or prevention of obesity. Therefore, the present invention can be utilized in pharmaceutical industries.

SEQUENCE LISTING FREE TEXT

Sequence 2: Synthetic RNA
Sequence 3: Synthetic RNA
Sequence 4: Synthetic RNA
Sequence 5: Synthetic RNA
Sequence 6: Synthetic RNA
Sequence 7: Synthetic RNA
Sequence 8: Primer
Sequence 9: Primer
Sequence 10: Primer
Sequence 11: Primer
Sequence 12: Primer
Sequence 13: Primer
Sequence 14: Primer
Sequence 15: Primer
Sequence 16: Primer
Sequence 17: Primer
Sequence 18: Primer
Sequence 19: Primer
Sequence 20: Primer
Sequence 21: Primer
Sequence 22: Primer
Sequence 23: Primer
Sequence 24: Primer
Sequence 25: Primer
Sequence 26: Primer
Sequence 27: Primer
Sequence 28: Primer
Sequence 29: Primer
Sequence 30: Primer
Sequence 31: Primer
Sequence 32: Primer
Sequence 33: Primer
Sequence 34: Primer
Sequence 35: Primer
Sequence 36: Primer
Sequence 37: Primer
Sequence 38: Primer
Sequence 39: Primer
Sequence 40: Primer
Sequence 41: Primer
Sequence 42: Primer
Sequence 43: Primer
Sequence 44: Primer

The invention claimed is:

1. A screening method for PGC-1β protein-function regulator, comprising:
  a step of causing a test substance to contact adipose tissue cells;
  a step of measuring or detecting a bond between synoviolin and PGC-1β protein in the adipose tissue cells after the test substance contacts the adipose tissue cells to decide whether the test substance inhibits a binding between synoviolin and PGC-1β; and
  a step of selecting the test substance as a candidate of PGC-1β protein-function regulator when the test substance is decided to inhibit the binding between synoviolin and PGC-1β,
  wherein the PGC-1β protein-function regulator inhibits binding between synoviolin and PGC-1β.

2. The method according to claim 1, further comprising a step of detecting the candidate of PGC-1B protein-function regulator as the therapeutic agent or the prevention agent for obesity.

* * * * *